US005712225A

United States Patent [19]

Hong et al.

[11] Patent Number: 5,712,225
[45] Date of Patent: Jan. 27, 1998

[54] OXA- AND THIA(DI)AZABICYCLIC COMPOUNDS

[75] Inventors: Wonpyo Hong, Hockessin, Del.; Matthias Schafer, Obernburg, Germany; Thomas Martin Stevenson, Newark, Del.

[73] Assignees: E. I. du Pont de Nemours and Company, Wilmington, Del.; Degussa Aktiengesellschaft, Frankfurt, Germany

[21] Appl. No.: 605,010

[22] PCT Filed: Aug. 30, 1994

[86] PCT No.: PCT/US94/09522

§ 371 Date: Feb. 28, 1996

§ 102(e) Date: Feb. 28, 1996

[87] PCT Pub. No.: WO95/06643

PCT Pub. Date: Mar. 9, 1995

[51] Int. Cl.$^6$ .................. C07D 498/02; A01N 43/824
[52] U.S. Cl. .................. 504/223; 504/221; 504/225; 504/266; 504/263; 504/267; 544/52; 544/66; 544/105; 544/133; 548/126; 548/154; 548/159; 548/161
[58] Field of Search .................. 544/66, 52, 105, 544/133; 504/223, 221, 225, 266, 267, 263; 548/126, 154, 161, 159

[56] References Cited

U.S. PATENT DOCUMENTS

| | | | |
|---|---|---|---|
| 4,437,877 | 3/1984 | Nagano et al. | 71/90 |
| 4,514,419 | 4/1985 | Cruickshank et al. | 514/521 |
| 4,684,397 | 8/1987 | Nagano et al. | 548/513 |
| 4,801,408 | 1/1989 | Nagano et al. | 564/218 |
| 4,816,063 | 3/1989 | Yamaguchi et al. | 544/232 |
| 4,885,023 | 12/1989 | Yamaguchi et al. | 544/235 |
| 5,039,331 | 8/1991 | Satow et al. | 71/90 |
| 5,108,486 | 4/1992 | Kondo et al. | 71/92 |
| 5,180,418 | 1/1993 | Pissiotas et al. | 504/193 |

FOREIGN PATENT DOCUMENTS

| | | |
|---|---|---|
| A-0 238 711 | 9/1987 | European Pat. Off. |
| A1 0 272 594 | 6/1988 | European Pat. Off. |
| A0 600 833 | 6/1994 | European Pat. Off. |
| 42 36 220 A1 | 4/1994 | Germany |
| WO 92/21684 | 12/1992 | WIPO |

OTHER PUBLICATIONS

S.K. Tsui et al., *Can. J. Chem.* 1979, 57(15), p. 1977.

M. Sekiya et al., *Chem. Lett.* 1982, (2), p. 231.

A. Klemann et al., *Die Pharmazie*, 46, No. 8, 573–575, 1991.

M. Sekiya et al., *Chem. Pharm. Bull.* 1983, 31(1), p. 94.

J.M. Cassal et al., *Helv. Chim. Acta* 1976, 59(6), p. 1917.

Primary Examiner—Joseph McKane

[57] ABSTRACT

The present invention relates to oxa(di)azabicyclic and thia(di)azabicyclic compounds, a method for their preparation and their use as herbicides.

5 Claims, No Drawings

OXA- AND THIA(DI)AZABICYCLIC COMPOUNDS

The present invention relates to novel oxa(di)azabicyclic and thia(di)azabicyclic compounds, a method for their preparation and their use as weedkillers.

As has already been reported, certain thiadiazabicyclic compounds (see EP 238 711, EP 304 920, U.S. Pat. Nos. 4,885,023, 4,684,397, US 4,801,408, WO 92/21684 and EP 600 833) can be used as weedkillers.

The present invention provides novel compounds of Formula I,

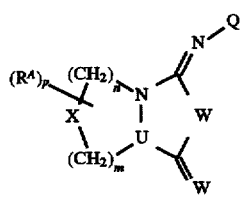

wherein:

X is selected from the group O, S, S(O), S(O)$_2$, CH$_2$, CHF, CF$_2$, CHCl, CHBr, CHOCH$_2$F, CHOCHF$_2$, CHOCF$_3$, CHOCH$_2$CF$_3$ and NR$^4$;

m and n are independently 1 or 2, where m+n=2 or 3;

p is 0 to 9;

U is N or CH;

W is independently O or S;

R$^A$ is independently selected from the group halogen, C$_1$–C$_4$ alkyl, cyano, C$_1$–C$_4$ haloalkyl, C$_3$–C$_4$ alkenyl, C$_1$–C$_3$ alkylthio, C$_1$–C$_3$ haloalkylthio, C$_2$–C$_4$ alkylcarbonyl, OR$^3$, C$_2$–C$_6$ alkyloxycarbonyl, C$_2$–C$_6$ haloalkoxycarbonyl, and C$_3$–C$_8$ alkoxycarbonylalkyl; or, two R$^A$ groups on the same carbon atom, together with this carbon, are C=O;

R$^3$ is selected from the group hydrogen, C$_1$–C$_4$ alkyl, C$_1$–C$_4$ haloalkyl, C$_2$–C$_4$ alkylcarbonyl and C$_2$–C$_4$ haloalkylcarbonyl;

R$^4$ is selected from the group hydrogen, C$_1$–C$_3$ alkyl, C$_1$–C$_3$ haloalkyl, C$_2$–C$_4$ alkylcarbonyl, C$_2$–C$_4$ haloalkoxycarbonyl and C$_2$–C$_4$ alkoxycarbonyl;

provided that:
  i) when X is CH$_2$ and U is N, then p is 1 to 8 and at least one R$^A$ is halogen; and
  ii) when X is CHOCH$_2$F, CHOCHF$_2$, CHOCF$_3$, or CHOCH$_2$CF$_3$, m and n are 1, and U is N, then p is 1 to 5 and at least one R$^A$ is other than alkyl;

Q is selected from the group

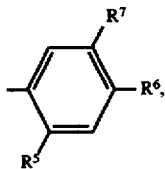   Q-1

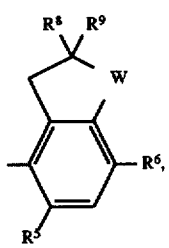   Q-2

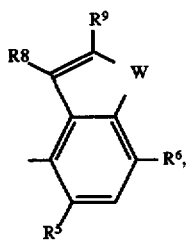   Q-3

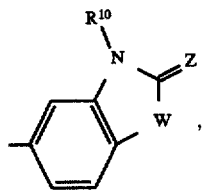   Q-4

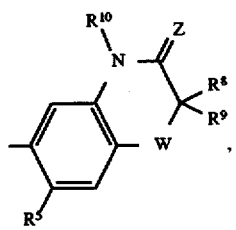   Q-5

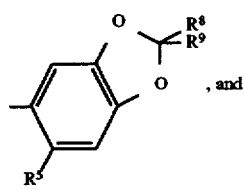   Q-6

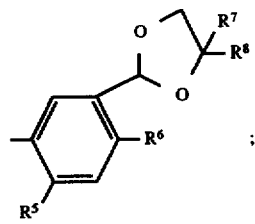   Q-7

Z is O or S;

R$^5$ is hydrogen or halogen;

R$^6$ is selected from the group C$_1$–C$_2$ alkyl, C$_1$–C$_2$ haloalkyl, OCH$_3$, SCH$_3$, OCHF$_2$, halogen, CN and NO$_2$;

R$^7$ is selected from the group hydrogen, C$_1$–C$_8$ alkyl, C$_1$–C$_8$ haloalkyl, halogen, OR$^{11}$, SR$^{11}$, S(O)$_q$R$^{11}$, COR$^{11}$, CO$_2$R$^{11}$, C(O)SR$^{11}$, C(O)NR$^{12}$R$^{13}$, CHO and NHSO$_2$NHR$^{16}$;

R$^8$ is selected from the group hydrogen, C$_1$–C$_3$ alkyl, C$_1$–C$_3$ haloalkyl and halogen;

R$^9$ is selected from the group hydrogen, C$_1$–C$_3$ alkyl, C$_1$–C$_3$ haloalkyl and halogen; or, when Q is Q-2 or Q-6, R$^8$ and R$^9$ together with the carbon to which they are bonded is additionally selected from C=O;

$R^{10}$ is selected from the group $C_1$–$C_6$ alkyl, $C_1$–$C_6$ haloalkyl, $C_2$–$C_6$ alkoxyalkyl, $C_3$–$C_6$ alkenyl and $C_3$–$C_6$ alkenyl;

$R^{11}$ is selected from the group $C_1$–$C_8$ alkyl, $C_3$–$C_8$ cycloalkyl, $C_3$–$C_8$ alkenyl, $C_3$–$C_8$ alkenyl, $C_1$–$C_8$ haloalkyl, $C_2$–$C_8$ alkoxyalkyl, $C_2$–$C_8$ alkylthioalkyl, $C_2$–$C_8$ alkylsulphinylalkyl, $C_2$–$C_8$ alkylsulphonylalkyl, $C_3$–$C_8$ alkoxyalkoxyalkyl, $C_4$–$C_8$ cycloalkylalkyl, $C_2$–$C_4$ carboxyalkyl, $C_3$–$C_8$ alkoxycarbonylalkyl, $C_6$–$C_8$ alkenyloxycarbonylalkyl, $C_6$–$C_8$ alkenyloxycarbonylalkyl, $C_5$–$C_8$ alkoxycarbonylalkenyl, $C_4$–$C_8$ alkenyloxyalkyl, $C_6$–$C_8$ cycloalkoxyalkyl, $C_4$–$C_8$ alkynyloxyalkyl, $C_3$–$C_8$ haloalkoxyalkyl, $C_4$–$C_8$ haloalkenyloxyalkyl, $C_4$–$C_8$ haloalkynyloxyalkyl, $C_4$–$C_8$ alkenylthioalkyl, $C_4$–$C_8$ alkynylthioalkyl; $C_1$–$C_4$ alkyl substituted with phenoxy or benzyloxy, each of the phenoxy and benzyloxy optionally substituted with at least one member independently selected from the group halogen, $C_1$–$C_3$ alkyl and $C_1$–$C_3$ haloalkyl, $C_4$–$C_8$ trialkylsilylalkyl, $C_3$–$C_8$ cyanoalkyl, $C_3$–$C_8$ halocycloalkyl, $C_3$–$C_8$ haloalkenyl, $C_5$–$C_8$ alkoxyalkenyl, $C_5$–$C_8$ haloalkoxyalkenyl, $C_5$–$C_8$ alkylthioalkenyl, $C_3$–$C_8$ haloalkynyl, $C_5$–$C_8$ alkoxyalkynyl, $C_5$–$C_8$ haloalkoxyalkynyl, $C_5$–$C_8$ alkylthioalkynyl, $C_2$–$C_8$ alkylcarbonyl; benzyl optionally substituted with at least one member independently selected from the group halogen, $C_1$–$C_3$ alkyl and $C_1$–$C_3$ haloalkyl; $CHR^{17}COR^{18}$, $CHR^{7}P(O)(ORJ^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl and pyridyl, each of the phenyl and pyridyl optionally substituted with at least one member independently selected from the group halogen, $C_1$–$C_3$ alkyl, $C_1$–$C_3$ haloalkyl, $C_1$–$C_4$ alkoxy and $CHR^{17}CH=NOR^{18}$;

$R^{12}$ and $R^{14}$ are independently hydrogen or $C_1$–$C_4$ alkyl;

$R^{13}$ and $R^{15}$ are independently selected from the group $C_1$–$C_4$ alkyl and phenyl optionally substituted with at least one member independently selected from the group halogen, $C_1$–$C_3$ alkyl, $C_1$–$C_3$ haloalkyl and $C_1$–$C_4$ alkoxy; or $R^{12}$ and $R^{13}$ are taken together as —$(CH_2)_5$—, —$(CH_2)_4$— or —$CH_2CH_2OCH_2CH_2$—, each independently forming a ring in which one or more H atoms is optionally replaced by at least one member independently selected from the group $C_1$–$C_3$ alkyl, optionally substituted phenyl and optionally substituted benzyl; or $R^{14}$ and $R^{15}$ together with the carbon atom to which they are attached is $C_3$–$C_8$ cycloalkyl;

$R^{16}$ is $C_1$–$C_4$ alkyl or $C_1$–$C_4$ haloalkyl;

$R^{17}$ is hydrogen or $C_1$–$C_3$ alkyl;

$R^{18}$ is selected from the group $C_1$–$C_6$ alkyl, $C_3$–$C_6$ alkenyl and $C_3$–$C_6$ alkynyl; and q is 1 or 2.

In the definitions given above the term 'alkyl', alone or in combined names such as 'alkylthio' or 'haloalkyl', includes a straight or branched chain isomers; for example, methyl, ethyl, n-propyl, isopropyl or the various butyl isomers. Alkoxy includes methoxy, ethoxy, n-propyloxy, isopropyl oxy and the various butyl oxy isomers. Alkenyl covers straight- or branch-chain alkenes; for example, 1-propenyl, 2-propenyl, 3-propenyl and the various butenyl isomers. Cycloalkyl includes cyclopropyl, cyclobutyl, cyclopentyl and cyclohexyl. The term 'halogen', alone or in combined names such as 'haloalkyl', signifies fluorine, chlorine, bromine or iodine. Furthermore, if 'haloalkyl' is used in the combined name, alkyl can be partly or totally substituted with halogen atoms, which in turn can be identical or different. Examples of haloalkyl are $CH_2CH_2F$, $CF_2CF_3$ and $CH_2CHFC_1$. Brackets in the nomenclature signify an optional component; for example, thia(di)azabicyclic compounds represent the aza- or the dim-compound.

Preference is given to the following radicals, wherein:

X is selected from the group O, CHF, $CF_2$ and CHCl;

$R^4$ is independently selected from the group fluorine, chlorine and bromine;

$R^5$ is selected from the group hydrogen, fluorine and chlorine;

$R^6$ is selected from the group chlorine, bromine and cyano;

$R^7$ is selected from the group hydrogen, $OR^{11}$, $CO_2R^{11}$, $C_1$–$C_2$ alkyl and $C_1$–$C_2$ haloalkyl;

$R^{10}$ is selected from the group $C_1$–$C_2$ alkyl, $C_1$–$C_2$ haloalkyl, $C_3$–$C_4$ alkenyl and $C_3$–$C_4$ alkynyl;

$R^{11}$ is selected from the group $C_1$–$C_4$ alkyl, $C_3$–$C_6$ cycloalkyl, $C_3$–$C_6$ alkenyl, $C_3$–$C_6$ alkynyl, $C_1$–$C_4$ haloalkyl, $C_2$–$C_4$ alkoxyalkyl, $C_2$–$C_4$ alkylthioalkyl, $C_2$–$C_4$ alkylsulphinylalkyl, $C_2$–$C_4$ alkylsulphonylalkyl, $C_3$–$C_6$ alkoxyalkoxyalkyl, $C_4$–$C_8$ cycloalkylalkyl, $C_2$–$C_4$ carboxyalkyl, $C_3$–$C_6$ alkoxycarbonylalkyl, $C_6$–$C_8$ alkenyloxycarbonylalkyl, $C_6$–$C_8$ alkynyloxycarbonylalkyl, $C_5$–$C_6$ alkoxycarbonylalkenyl, $C_6$–$C_8$ cycloalkoxyalkyl, $C_4$–$C_6$ alkenyloxyalkyl, $C_4$–$C_6$ alkynyloxyalkyl, $C_3$–$C_6$ haloalkoxyalkyl, $C_4$–$C_8$ haloalkenoxyalkyl, $C_4$–$C_6$ haloalkynyloxyalkyl, $C_6$–$C_8$ cycloalkylthioalkyl, $C_4$–$C_6$ alkenylthioalkyl, $C_4$–$C_6$ alkynylthioalkyl; $C_1$–$C_2$ alkyl substituted with phenoxy or benzyloxy, each of the phenoxy and benzyloxy optionally substituted with at least one member independently selected from the group halogen, $C_1$–$C_3$ alkyl and $C_1$–$C_3$ haloalkyl; $C_4$–$C_8$ trialkylsilylalkyl, $C_3$–$C_4$ cyanoalkyl, $C_3$–$C_6$ halocycloalkyl, $C_3$–$C_6$ haloalkenyl, $C_5$–$C_6$ alkoxyalkenyl, $C_5$–$C_6$ haloalkoxyalkenyl, $C_5$–$C_6$ alkylthioalkenyl, $C_3$–$C_6$ haloalkynyl, $C_5$–$C_6$ alkoxyalkynyl, $C_5$–$C_6$ haloalkoxyalkynyl, $C_5$–$C_6$ alkylthioalkynyl, $C_2$–$C_4$ alkylcarbonyl, benzyl optionally substituted with at least one member independently selected from the group halogen, $C_1$–$C_2$ alkyl and $C_1$–$C_2$ haloalkyl; $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl and pyridyl, each of the phenyl and pyridyl optionally substituted with at least one member independently selected from the group fluorine, chlorine, bromine, $C_1$–$C_2$ alkylhaloalkyl and $C_1l\propto C_2$ alkoxy;

$R^{12}$ is hydrogen or $C_1$–$C_2$ alkyl;

$R^{13}$ is selected from the group $C_1$–$C_2$ alkyl and phenyl optionally substituted with at least one member selected from the group fluorine, chlorine, bromine, $C_1$–$C_2$ alkyl, $C_1$–$C_2$ haloalkyl and $C_1$–$C_2$ alkoxy; or $R^{12}$ and $R^{13}$ are taken together as —$(CH_2)_5$—, —$(CH_2)_4$— or —$CH_2CH_2OCH_2CH_2$—, each independently forming a ring in which one or more H atoms is optionally and independently replaced by $C_1$–$C_2$ alkyl;

$R^{17}$ is hydrogen or $C_1$–$C_2$ alkyl; and $R^{18}$ is selected from the group $C_1$–$C_2$ alkyl, $C_3$–$C_4$ alkenyl and $C_3$–$C_4$ alkynyl.

Compounds of Formula I can exist as one or more stereoisomers. The various stereoisomers comprise enantiomers, diastereomers and geometric isomers. The skilled person knows that a stereoisomer may be more active and how the cited enantiomers, diastereomers and geometric isomers can be separated. Accordingly, the present invention covers racemic mixtures, individual stereoisomers and optically active mixtures of compounds of Formula I.

The novel oxa- or thiaazabicyclic compounds of general Formula Ia,

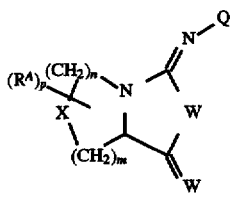   Ia wherein n, m, p, X, W, $R^4$ and Q have the meanings given above, are obtained according to the present invention by reacting an aryliso(thio)cyanate of Formula II,

Q-NCW   II wherein W and Q have the meanings given above, with a (thio)carboxylic acid or ester of Formula III,

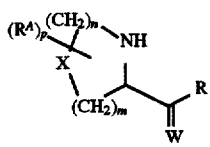   III wherein n, m, p, X, W, and $R^4$ have the meanings given above and R represents hydroxy, $C_1$–$C_4$ alkoxy, halogen or O-active esters, for example O-succinimide esters or anhydrides (see Houben-Weyl, Vol. 25/1 and 25/2 (1974)) optionally in the presence of an acid acceptor and a diluent.

The invention also provides a method for preparation of compounds of Formula I by reacting a compound of Formula IV,

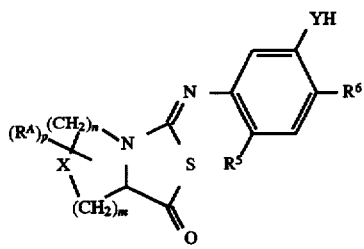   IV wherein n, m, p, X, $R^4$, $R^5$ and $R^6$ have the meanings given above and Y=O, S, or NH, with an electrophile of Formula V, VI or VII, $R^{11}$—Z   V
$R^{16}SO_2$—Z   VI
$R^{16}NHSO_2$—Z   VII wherein Z is a chlorine, bromine or iodine atom or O—$SO_2CH_3$, O—$SO_2CF_3$, O—$SO_2$—Ph, O—$SO_2$-(4-methylphenyl) and $R^{11}$ and $R^{16}$ have the meanings given above.

The invention also provides a method for preparation of compounds of Formula I, wherein m, n, p, X, $R^4$, W and Q have the meanings given above, comprising reacting a compound of Formula III, wherein R is hydroxy, ($C_1$–$C_4$) alkoxy, halogen or O-active ester, with thiophosgene or with a thiophosgene-substitute XV, wherein $L_1$ and $L_2$ are independently appropriate leaving groups, to produce compounds of Formula VIII, which are then reacted with compounds of Formula IX to form compounds of Formula X,

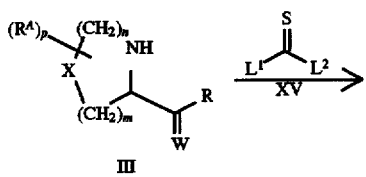   III

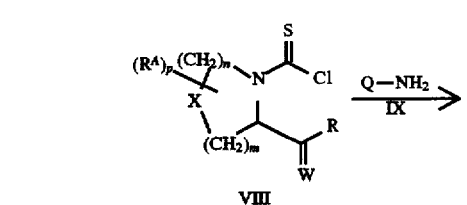   VIII

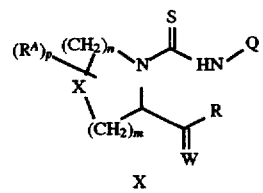   X and, finally, convening the compounds of Formula X to compounds of Formula I by cyclization.

The invention also provides a method for preparation of compounds of Formula Ib

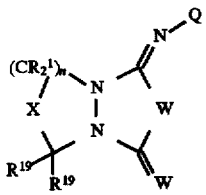   Ib wherein n, W and Q have the meanings given above and $R^1$, $R^{19}$ and X have the meanings given below, by reacting a compound of Formula XI,

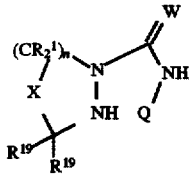   XI wherein X is O, S, or $NR^4$, $R^1$ is independently $R^4$ or hydrogen, and $R^{19}$ is independently selected from the group hydrogen, $C_1$–$C_4$ alkyl, $C_1$–$C_4$ haloalkyl or $C_3$–$C_4$ alkenyl, with a compound of Formula XVb, $CWCl_2$   XVb wherein W has the meaning given above, preferably in an inert organic solvent, for example in an aromatic solvent such as toluene or chlorobenzene, in a halogensted hydrocarbon such as chloroform or methylene chloride, in an ether such as diisopropylether or in acetonitrile or dimethylformamide, preferably by means of base catalysis and preferably at temperatures of 0°–120° C. Bases or organic bases, for example organic amines such as triethylamine, are preferably used, but pyridine may also be used, preferably in the presence of activate$_d$ charcoal.

Compounds of Formula XI can be obtained by reacting compounds of Formula XIII,

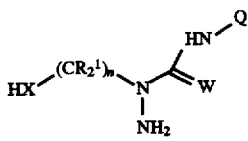

wherein X is O, S, or NR⁴, and n, R¹, R⁴, W and Q have the meanings given above, with ketones or aldehydes of Formula XII

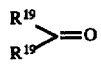

or with phosgene or a phosgene substitute. In Formula XII, $R^{19}$ has the meaning given above. C=O is obtained in the ring upon reaction with phosgene or phosgene substitute. The reaction is preferably carried out in an inert organic solvent, for example in an aromatic solvent such as toluene or chlorobenzene, a halogenated hydrocarbon such as chloroform or methylene chloride, an ether such as diisopropylether or in acetonitrile or dimethylformamide, preferably by means of acid catalysis and preferably at temperatures of 20°–120° C. Preferred acids are organic acids, for example organic sulfonic acids such as p-toluenesulfonic acid.

Compounds of Formula XII are obtained by reacting 2-mercapto-, 2-hydroxyalkylhydrazines or 2-aminoalkylhydrazines of Formula XIV,

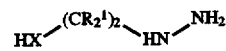

wherein X is O, S, or NR⁴ and R¹ and R⁴ have the meanings given above, with aryliso(thio)cyanates of Formula II, wherein Q has the meaning given above, preferably in an inert organic solvent, for example in an aromatic solvent such as toluene or chlorobenzene, in a halogensted hydrocarbon such as chloroform or methylene chloride, in an ether such as diisopropylether or in acetonitrile or dimethylformamide or alcohols, such as methanol or ethanol, preferably by means of base catalysis and preferably at temperatures of 20°–120° C. Bases or organic bases, for example organic amines such as triethylamine, but also pyridine, are preferably used.

In the reaction of a compound of Formula II with a compound of Formula III when R=alkyl, the reaction is carried out in an inert organic solvent, for example in an aromatic solvent such as toluene or chlorobenzene, in a halogenated hydrocarbon such as chloroform or methylene chloride, in an ether such as diisopropylether or tetrahydrofuran or in acetonitrile or dimethylformamide, optionally with base catalysis at temperatures between –20° C. and 125° C. Organic bases, for example organic amines such as triethylamine or even pyridine or also for example inorganic bases such as potassium carbonate (see EP-A10 272 594) are preferably used as bases. Variants of the general method A are described in EP-A2 0 070 389.

In the case where R=hydroxy, the reaction is carried out in water or methanol as solvent or, preferably, in a biphasic water/organic solvent system. Particular preference is given to the method in which a compound of Formula III, optionally salts of III, is added in water together with an inorganic base, for example an alkali- or alkaline earth metal hydroxide, carbonate or bicarbonate such as sodium hydrolide or potassium carbonate, or together with an organic base, for example, an organic amine such as triethylamine, followed by addition of compounds of Formula II dissolved in an inert solvent, for example, toluene, chlorobenzene or chloroform. Compounds II can, if necessary, also be added directly to the aqueous or alcoholic solution. The reaction mixture is then kept for several days, preferably for between 3 and 50 hours, at temperatures of between –40° C. and +50° C., preferably between –10° C. and +30° C.

The aqueous phase is then adjusted to a pH between 1 and 3 with acid, preferably an inorganic acid such as aqueous hydrochloric or sulphuric acid. The thiourea derivatives (see compounds X) thus produced are then cyclized at temperatures of between 0° C. and 100° C., optionally in the presence of an acid such as hydrochloric acid and/or formic acid, or with the aid of a dehydrating substance, for example, dicyclohexylcarbodiimide (DCC), in a solvent known to the skilled person (for example, acetonitrile), or optionally by conversion into an ester (R=alkyl or active ester) by known methods (see Houben-Weyl, *Methoden der organischen Chemie*, Vol. XV (1974)).

The compounds of Formula II are known or can be prepared by known methods; for these see EP 304 920, EP 238 711, EP 409 025, EP 373 461, EP 311 135 and DE 37 24 096.

Amines of Formula III are known and can be prepared by the known methods; for these see for example M. Sekiya et al., *Chem. Pharm. Bull.* (1983), 31(1), p 94; J. M. Cassal, A. Furst, W. Meier. *Helv. Chim. Acta* (1976), 59(6), p 1917; S.-K. Tsui, J. D. Wood, *Can. J. Chem.* (1979), 57(15), p 1977; M. Sekiya et al., *Chem. Lett.* (1982), (2), p 231.

EXAMPLE 1

N-Amino-N-(2-hydroxyethyl)-N'-(2 4-dichlorophenyl)thiourea 7.61 g (0.10 mol) 2-hydroxyethylhydrazine was dissolved in 100 mL methylene chloride at 0°–5° C. After dropwise addition of 10.2 g (0.10 tool) triethylamine, 20.4 g (0.10 mol) 2,4-dichlorophenylisothiocyanate dissolved in 70 mL methylene chloride was added over a period of 4 h. The reaction mixture was left to warm up to room temperature, stirred for a further 2 h, the precipitate filtered off, washed with methylene chloride and the desired compound isolated.

EXAMPLE 2

N-(2,4-Dichlorophenyl)tetrahydro-4H-1,3,4-oxadiazine-4-carbothioamide

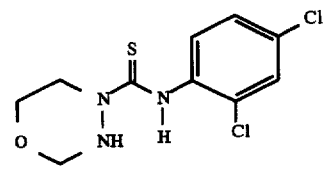

1.72 g (6.20 mmol) N-amino-N-(2-hydroxyethyl)-N'-(2,4-dichlorophenyl)thiourea was suspended in 40 mL methylene chloride. 0.52 g (37% aqueous, 6.4 mmol) formaldehyde and a small quantity of p-toluenesulfonic acid were added before the reaction mixture was heated for 17 h in a Dean-Stark apparatus. The solvent was then removed and the desired product isolated.

EXAMPLE 3

1-[(2,4-Dichlorophenyl)imino]dihydro-1H,3H,5H-[1,3,4]thiadiazolo[3,4-c]-[1,3,4]oxadiazin-3-one

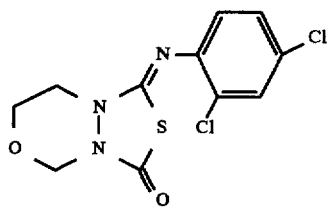

1.8 g (6.2 mmol) N-(2,4-dichlorophenyl)tetrahydro-4H-1,3,4-oxadiazine-4-carbothioamide was dissolved in 30 mL toluene and 1 mL triethylamine in the presence of a small quantity of activated charcoal at 0°–5° C. 3.49 g (6.81 mmol) phosgene as 20% solution in 30 mL toluene was added dropwise over 1.5 h. The reaction mixture was then left to warm up to room temperature and stirred overnight. The activated charcoal was removed by filtration and the solvent evaporated in vacuo. The desired product was isolated after chromatography on silica gel.

EXAMPLE 4

3-[[4-Chloro-2-fluoro-5-(1-methylethoxy)phenyl]imino]-6-fluorotetrahydro-1H,3H-pyrrolo[1,2-c]thiazol-1-one

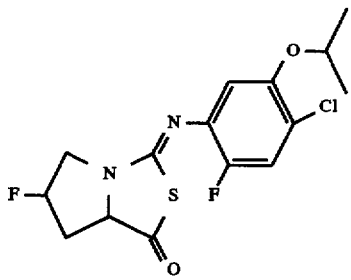

A mixture of 1.31 g (0.01 mol) 4-fluoroproline, 30 mL 2N KOH in methanol and 10 mL water is prepared before 2.46 g (0.01 mol) 4-chloro-2-fluoro-5-isopropoxyphenylisothiocyanate dissolved in 250 mL methanol is added dropwise. The reaction mixture is stirred overnight at room temperature, the aqueous phase adjusted to pH 2 and the resultant product (3.77 g. See Formula X) is filtered. The compound thus obtained is dissolved in 50 mL acetonitrile before 2.59 g (0.01 mol) dicyclohexylcarbodiimide is added at room temperature. The reaction mixture is stirred for 3 h and the crude product is purified by silica gel chromatography to give 3.24 g (85% yield) of the desired product.

EXAMPLE 5

3-[[4-Chloro-2-fluoro-5-(propynyloxy)phenyl]imino]-6-fluorotetrahydro-1H,3H-pyrrolo[1,2c]thiazol-1-one

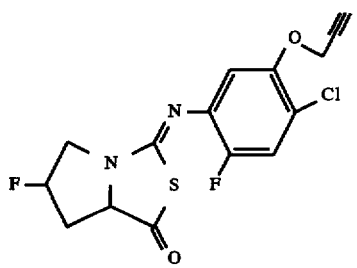

A mixture of 3.18 g (0.01 tool) 3-[[4-chloro-2-fluoro-5-(1-methylethoxy)phenyl]-imino]-6-fluorotetrahydro-1H,3H-pyrrolo[1,2-c]thiazol-1-one, 6.95 g (0.05 tool) potassium carbonate, 1.78 g (12.0 mmol) propargyl bromide and 60 mL acetonitrile is stirred for 20 h at room temperature. The reaction mixture is adjusted to pH 2 with 5% aqueous hydrochloric acid and extracted with diethylether (3×15 mL). The organic phase is then dried, the solvent distilled off in vacuo and the crude product purified on a silica gel column.

TABLE 1

| $R^1$ | $R^1$ | $R^5$ | $R^6$ | $R^7$ | X |
|---|---|---|---|---|---|
| H | H | F | Cl | H | O |
| H | H | F | Cl | $CO_2CH(CH_3)_2$ | O |
| H | H | F | Cl | $CO_2CH_3$ | O |
| H | H | F | Cl | $CO_2C_2H_5$ | O |
| H | H | F | Cl | $CO_2CH(CH_3)CF_3$ | O |
| H | H | F | Cl | $CO_2CH_2CH_2CH_3$ | O |
| H | H | F | Cl | $CO_2CH(CH_3)CH_2CH_3$ | O |
| H | H | F | Cl | $CO_2CH_2CH(CH_3)_2$ | O |
| H | H | F | Cl | $CO_2CH_2C\equiv CH$ | O |
| H | H | F | Cl | $CO_2CH(CH_3)C\equiv CH$ | O |
| H | H | F | Cl | $CO_2CH_2CF_3$ | O |
| H | H | F | Cl | $CON(CH_3)_2$ | O |
| H | H | F | Cl | $CO_2CH(CH_3)CO_2C_2H_5$ | O |
| H | H | F | Cl | $OCH_3$ | O |
| H | H | F | Cl | $OCH(CH_3)_2$ | O |
| H | H | F | Cl | $OCH_2C\equiv CH$ | O |
| H | H | F | Cl | $OCH(CH_3)C\equiv CH$ | O |
| H | H | F | Cl | $OCH_2C(O)N(CH_3)_2$ | O |
| H | H | F | Cl | $OCH_2P(O)(OC_2H_5)_2$ | O |
| H | H | F | Cl | $OCH_2P(S)(OC_2H_5)_2$ | O |
| H | H | F | Cl | $OCF_2CHFCl$ | O |
| H | H | F | Cl | $OCHF_2$ | O |
| H | H | F | Cl | $OCH_2CH=CH_2$ | O |
| H | H | F | Cl | $OCH_2CH=CHCl$ | O |
| H | H | F | Cl | $OCH_2C(Cl)=CH_2$ | O |
| H | H | F | Cl | $SCH_2CO_2H$ | O |
| H | H | F | Cl | $SCH_2CO_2CH_3$ | O |
| H | H | F | Cl | $NHSO_2CH_3$ | O |

TABLE 1-continued

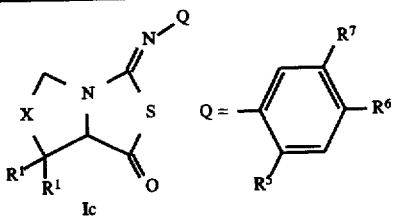

Ic

| R¹ | R¹ | R⁵ | R⁶ | R⁷ | X |
|---|---|---|---|---|---|
| H | H | F | Cl | NHSO₂CF₃ | O |
| H | H | F | Cl | NHSO₂CH(CH₃)₂ | O |
| H | H | F | Cl | NHSO₂NHCH₃ | O |
| H | H | H | Cl | H | CHF |
| H | H | F | Cl | H | CHF |
| H | H | F | Cl | CO₂CH(CH₃)₂ | CHF |
| H | H | F | Cl | CO₂CH₃ | CHF |
| H | H | F | Cl | CO₂C₂H₅ | CHF |
| H | H | F | Cl | CO₂CH(CH₃)CF₃ | CHF |
| H | H | F | Cl | CO₂CH₂CH₂CH₃ | CHF |
| H | H | F | Cl | CO₂CH(CH₃)CH₂CH₃ | CHF |
| H | H | F | Cl | CO₂CH₂CH(CH₃)₂ | CHF |
| H | H | F | Cl | CO₂CH₂C≡CH | CHF |
| H | H | F | Cl | CO₂CH(CH₃)C≡CH | CHF |
| H | H | F | Cl | CO₂CH₂CF₃ | CHF |
| H | H | F | Cl | CON(CH₃)₂ | CHF |
| H | H | F | Cl | CO₂CH(CH₃)CO₂C₂H₅ | CHF |
| H | H | F | Cl | OCH₃ | CHF |
| H | H | F | Cl | OCH(CH₃)₂ | CHF |
| H | H | F | Cl | OCH₂C≡CH | CHF |
| H | H | F | Cl | OCH(CH₃)C≡CH | CHF |
| H | H | F | Cl | OCH₂C(O)N(CH₃)₂ | CHF |
| H | H | F | Cl | OCH₂P(O)(OC₂H₅)₂ | CHF |
| H | H | F | Cl | OCH₂P(S)(OC₂H₅)₂ | CHF |
| H | H | F | Cl | OCF₂CHFCl | CHF |
| H | H | F | Cl | OCHF₂ | CHF |
| H | H | F | Cl | OCH₂CH=CH₂ | CHF |
| H | H | F | Cl | OCH₂CH=CHCl | CHF |
| H | H | F | Cl | OCH₂C(Cl)=CH₂ | CHF |
| H | H | F | Cl | CN | CHF |
| H | H | F | Cl | SCH₂CO₂H | CHF |
| H | H | F | Cl | SCH(CH₃)₂ | CHF |
| H | H | F | Cl | SCH₂CO₂CH₃ | CHF |
| H | H | F | Cl | SCH₂C≡CH | CHF |
| H | H | F | Cl | NHSO₂CH₃ | CHF |
| H | H | F | Cl | NHSO₂CF₃ | CHF |
| H | H | F | Cl | NHSO₂CH(CH₃)₂ | CHF |
| H | H | F | Cl | NHSO₂NHCH₃ | CHF |
| H | H | F | Cl | OCH₂CO₂C₅H₁₁ | CHF |
| H | H | F | Cl | OCH₂CH=N—OCH₃ | CHF |
| H | H | F | Cl | OCH₂CH=N—OCH₂CH=CH₂ | CHF |
| H | H | F | Cl | OCH₂Si(CH₃)₃ | CHF |
| H | H | F | Cl | OCH₂C(O)N⟨—O⟩ (morpholine) | CHF |
| H | H | Cl | Cl | CO₂CH(CH₃)₂ | CHF |
| H | H | Cl | Cl | OCH₂C≡CH | CHF |
| H | H | Cl | Cl | CO₂CH(CH₃)C₂H₅ | CHF |
| H | H | CN | Cl | CO₂CH(CH₃)₂ | CHF |
| H | H | CN | Cl | CO₂CH(CH₃)C₂H₅ | CHF |
| F | H | F | Cl | CO₂CH(CH₃)₂ | CH₂ |
| F | H | F | Cl | CO₂CH(CH₃)C₂H₅ | CH₂ |
| F | H | F | Cl | CO₂CH₂CH₂CCl₃ | CH₂ |
| F | H | F | Cl | OCH₂C≡CH | CH₂ |
| F | H | F | Cl | OCH(CH₃)C≡CH | CH₂ |
| F | H | F | Cl | OCH(CH₃)₂ | CH₂ |
| F | H | F | Cl | CO₂CH₃ | CH₂ |
| F | H | F | Cl | SCH₂CO₂H | CH₂ |
| H | H | Cl | Cl | H | CH₂ |
| H | H | Cl | Cl | Cl | CH₂ |
| F | H | F | Cl | CO₂C₂H₅ | CH₂ |
| F | H | F | Cl | SCH₂CO₂Me | CH₂ |
| F | H | F | Cl | NHSO₂CH₃ | CH₂ |
| F | H | F | Cl | NHSO₂C₂H₅ | CH₂ |
| H | H | F | Cl | CO₂CH₃ | CHCl |
| H | H | F | Cl | CO₂C₂H₅ | CHCl |
| H | H | F | Cl | CO₂CH(CH₃)₂ | CHCl |
| H | H | F | Cl | CO₂CH(CH₃)C₂H₅ | CHCl |
| H | H | F | Cl | CO₂CH₂CH₂CH₃ | CHCl |
| H | H | F | Cl | CO₂CH₂CH(CH₃)₂ | CHCl |
| H | H | F | Cl | SCH₂CO₂Me | CHCl |
| H | H | F | Cl | OCH(CH₃)₂ | CHCl |
| H | H | F | Cl | SCH₂CO₂H | CHCl |
| H | H | F | Cl | OCH₂C≡CH | CHCl |
| H | H | F | Cl | OCH(CH₃)C≡CH | CHCl |
| H | H | F | Cl | NHSO₂CH₃ | CHCl |
| H | H | F | Cl | NHSO₂C₂H₅ | CHCl |
| H | H | F | Cl | CO₂CH(CH₃)₂ | CHBr |
| H | H | F | Cl | CO₂CH(CH₃)CH₂CH₃ | CHBr |
| H | H | F | Cl | OCH₃ | CHBr |
| H | H | F | Cl | OCH(CH₃)₂ | CHBr |
| H | H | F | Cl | OCH₂C≡CH | CHBr |
| H | H | F | Cl | OCH(CH₃)C≡CH | CHBr |
| H | H | F | Cl | OCH₂CH=CH₂ | CHBr |
| H | H | F | Cl | SCH₂CO₂Me | CHBr |
| H | H | F | Cl | CO₂CH(CH₃)₂ | CHOCHF₂ |
| H | H | F | Cl | CO₂CH(CH₃)CH₂CH₃ | CHOCHF₂ |
| H | H | F | Cl | OCH₃ | CHOCHF₂ |
| H | H | F | Cl | OCH(CH₃)₂ | CHOCHF₂ |
| H | H | F | Cl | OCH₂C≡CH | CHOCHF₂ |
| H | H | F | Cl | OCH(CH₃)C≡CH | CHOCHF₂ |
| H | H | F | Cl | OCH₂CH=CH₂ | CHOCHF₂ |
| H | H | F | Cl | CO₂CH(CH₃)₂ | CHOCF₃ |
| H | H | F | Cl | CO₂CH(CH₃)CH₂CH₃ | CHOCF₃ |
| H | H | F | Cl | OCH₃ | CHOCF₃ |
| H | H | F | Cl | OCH(CH₃)₂ | CHOCF₃ |
| H | H | F | Cl | OCH₂C≡CH | CHOCF₃ |
| H | H | F | Cl | OCH(CH₃)C≡CH | CHOCF₃ |
| H | H | F | Cl | OCH₂CH=CH₂ | CHOCF₃ |
| H | H | F | Cl | CO₂CH(CH₃)₂ | CHOCH₂CF₃ |
| H | H | F | Cl | CO₂CH(CH₃)CH₂CH₃ | CHOCH₂CF₃ |
| H | H | F | Cl | OCH₃ | CHOCH₂CF₃ |
| H | H | F | Cl | OCH(CH₃)₂ | CHOCH₂CF₃ |
| H | H | F | Cl | OCH₂C≡CH | CHOCH₂CF₃ |
| H | H | F | Cl | OCH(CH₃)(C≡CH | CHOCH₂CF₃ |
| H | H | F | Cl | OCH₂CH=CH₂ | CHOCH₂CF₃ |

TABLE 2

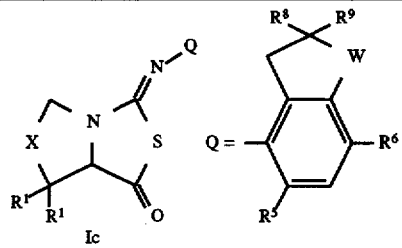

| R¹ | R¹ | R⁵ | R⁶ | R⁸ | R⁹ | X | W |
|---|---|---|---|---|---|---|---|
| H | H | F | Cl | H | CH₃ | O | O |
| H | H | F | Cl | H | CH₃ | CHF | O |
| H | H | F | Cl | CH₃ | CH₃ | CHF | O |
| H | H | F | Cl | H | CH₂F | CHF | O |
| H | H | F | Cl | H | CH₂Cl | CHF | O |
| H | H | F | Cl | H | CH₂Br | CHF | O |
| H | H | F | Cl | H | CH(CH₃)₂ | CHF | O |
| H | H | F | Cl | H | CH₂CH₃ | CHF | O |
| H | H | F | Br | H | CH₃ | CHF | O |
| H | H | F | OCH₃ | H | CH₃ | CHF | O |
| H | H | F | CH₃ | H | CH₃ | CHF | O |
| H | H | F | CN | H | CH₃ | CHF | O |
| H | H | F | CF₃ | H | CH₃ | CHF | O |
| H | H | F | OCHF₂ | H | CH₃ | CHF | O |
| H | H | F | Cl | H | CH₃ | CHF | S |
| H | H | F | Cl | H | CH₃ | O | S |
| F | H | F | Cl | H | CH₃ | CH₂ | O |
| H | H | F | Cl | H | CH₃ | CHCl | O |
| F | H | F | Cl | H | CH₃ | CH₂ | S |
| H | H | F | Cl | H | CH₃ | CHCl | S |
| H | H | F | Cl | H | CH₃ | CHBr | O |
| H | H | F | Cl | H | CH₃ | CHOCHF₂ | O |
| H | H | F | Cl | H | CH₃ | CHOCF₃ | O |
| H | H | F | Cl | H | CH₃ | CHOCH₂CF₃ | O |

TABLE 3

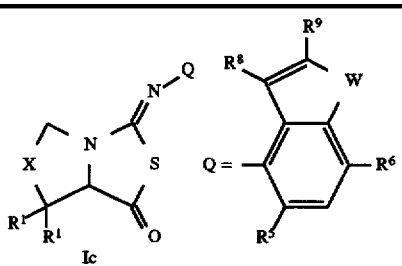

| R¹ | R¹ | R⁵ | R⁶ | R⁸ | R⁹ | X | W |
|---|---|---|---|---|---|---|---|
| H | H | F | Cl | H | Cl | O | S |
| H | H | F | Cl | H | CH₃ | O | S |
| H | H | F | Cl | H | H | CHF | S |
| H | H | F | Cl | H | Cl | CHF | S |
| H | H | F | Cl | CH₃ | CH₃ | CHF | S |
| H | H | H | SCH₃ | H | H | CHF | S |
| H | H | F | Cl | H | Cl | CHCl | S |
| F | H | F | Cl | H | Cl | CH₂ | S |
| H | H | F | Cl | H | CH₃ | CHCl | S |
| F | H | F | Cl | H | CH₃ | CH₂ | S |
| H | H | F | Cl | H | Cl | CHF | O |
| H | H | F | Cl | H | H | CHF | O |
| H | H | F | Cl | H | CH₃ | CHF | O |
| H | H | F | Cl | H | C₂H₅ | CHF | S |
| H | H | F | Cl | H | Cl | CHBr | S |
| H | H | F | Cl | H | CH₃ | CHBr | S |
| H | H | F | Cl | H | Cl | CHOCHF₂ | S |
| H | H | F | Cl | H | CH₃ | CHOCHF₂ | S |
| H | H | F | Cl | H | Cl | CHOCF₃ | S |

TABLE 3-continued

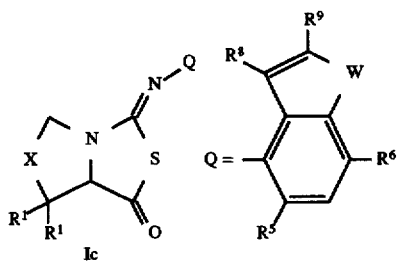

| R¹ | R¹ | R⁵ | R⁶ | R⁸ | R⁹ | X | W |
|---|---|---|---|---|---|---|---|
| H | H | F | Cl | H | CH₃ | CHOCF₃ | S |
| H | H | F | Cl | H | Cl | CHOCH₂CF₃ | S |

TABLE 4

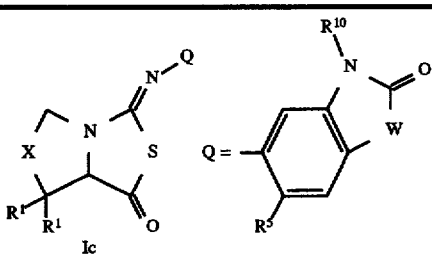

| R¹ | R¹ | R⁵ | R¹⁰ | X | W |
|---|---|---|---|---|---|
| H | H | F | CH₂C≡CH | O | S |
| H | H | F | CH₂CH=CH₂ | O | S |
| H | H | F | H | CHF | S |
| H | H | F | CH₃ | CHF | S |
| H | H | F | CH₂C≡CH | CHF | S |
| H | H | F | CH(CH₃)C≡CH | CHF | S |
| H | H | F | CH₂CH=CH₂ | CHF | S |
| H | H | F | CH₂OCH₃ | CHF | S |
| H | H | F | CH(CH₃)₂ | CHF | S |
| H | H | F | CHF₂ | CHF | S |
| H | H | F | CF₂CHF₂ | CHF | S |
| H | H | F | CH₂CH=CHCH₃ | CHF | S |
| H | H | F | CH₂CH₂CH₃ | CHF | S |
| H | H | F | CH₂C≡CH | CHF | O |
| H | H | F | CH₂CH=CH₂ | CHF | O |
| H | H | Cl | CH₂C≡CH | CHF | S |
| F | H | F | CH₂C≡CH | CHF | S |
| F | H | F | CH₂CH=CH₂ | CHF | S |
| H | H | F | CH₂C≡CH | CHCl | S |
| H | H | F | CH₂CH=CH₂ | CHCl | S |
| H | H | F | CH₃ | CHCl | S |
| H | H | F | CH₂C≡CH | CHBr | S |
| H | H | F | CH₂CH=CH₂ | CHBr | S |
| H | H | F | CH₂C≡CH | CHBr | O |
| H | H | F | CH₂C≡CH | CHOCHF₂ | S |
| H | H | F | CH₂C≡CH | CHOCF₃ | S |
| H | H | F | CH₂C≡CH | CHOCH₂CF₃ | S |

TABLE 5

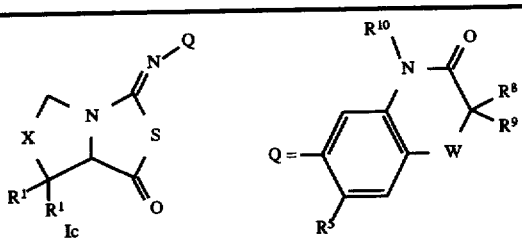

| R¹ | R¹ | R⁵ | R⁸ | R⁹ | R¹⁰ | X | W |
|---|---|---|---|---|---|---|---|
| H | H | F | H | H | CH₂C≡CH | O | O |
| H | H | F | H | H | CH₂CH=CH₂ | O | O |
| H | H | F | H | H | CH₃ | O | O |
| H | H | H | H | H | CH₃ | CHF | O |
| H | H | H | H | H | CH₂C≡CH | CHF | O |
| H | H | F | H | H | CH₃ | CHF | O |
| H | H | F | H | H | C₂H₅ | CHF | O |
| H | H | F | H | H | CH(CH₃)₂ | CHF | O |
| H | H | F | H | H | CH₂CH₂CH₃ | CHF | O |
| H | H | F | H | H | CH₂CH=CH₂ | CHF | O |
| H | H | F | H | H | CH₂C≡CH | CHF | O |
| H | H | F | H | H | CH(CH₃)C≡CH | CHF | O |
| H | H | H | H | H | CH₂C≡CH | CHF | S |
| H | H | F | H | H | CH₂C≡CH | CHF | S |
| H | H | Cl | H | H | CH₂C≡CH | CHF | O |
| H | H | F | H | CH₃ | CH₂C≡CH | CHF | O |
| F | H | H | H | H | CH₂C≡CH | CH₂ | O |
| F | H | F | H | H | CH₃ | CH₂ | O |
| F | H | F | H | H | CH₂C≡CH | CH₂ | O |
| F | H | F | H | H | CH₂CH=CH₂ | CH₂ | O |
| H | H | H | H | H | CH₂C≡CH | CHCl | O |
| H | H | F | H | H | CH₃ | CHCl | O |
| H | H | F | H | H | CH₂C≡CH | CHCl | O |
| H | H | F | H | H | CH₂—CH=CH₂ | CHCl | O |
| H | H | F | H | H | CH₂CH=CH₂ | CHCl | S |
| H | H | F | H | H | CH₂C≡CH | CHBr | O |
| H | H | F | H | H | CH₂C≡CH | CHBr | S |
| H | H | F | H | H | CH₂CH=CH₂ | CHBr | O |
| H | H | F | H | H | CH₂C≡CH | CHOCHF₂ | O |
| H | H | F | H | H | CH₂C≡CH | CHOCF₃ | O |
| H | H | F | H | H | CH₂C≡CH | CHOCH₂CF₃ | O |

TABLE 6

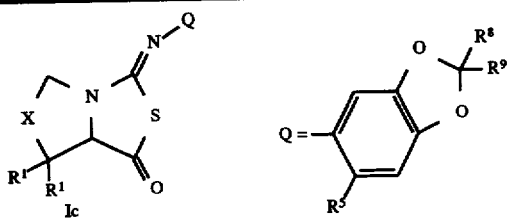

| R¹ | R¹ | R⁵ | R⁸ | R⁹ | X |
|---|---|---|---|---|---|
| H | H | H | F | F | O |
| H | H | F | F | F | O |
| H | H | F | H | H | O |
| H | H | F | F | F | CHF |
| H | H | F | F | H | CHF |
| F | H | F | F | F | CH₂ |
| F | H | F | F | F | CH₂ |
| F | H | F | H | H | CH₂ |
| H | H | H | F | F | CHCl |
| H | H | F | F | F | CHCl |
| H | H | F | H | H | CHCl |
| H | H | F | F | F | CHBr |
| H | H | F | F | F | CHBr |
| H | H | F | H | H | CHBr |
| H | H | F | F | F | CHOCHF₂ |
| H | H | F | F | F | CHOCF₃ |
| H | H | F | F | F | CHOCH₂CF₃ |

TABLE 7

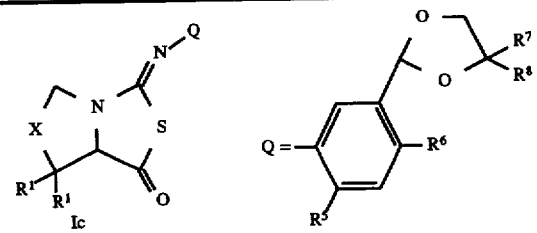

| R¹ | R¹ | R⁵ | R⁶ | R⁷ | R⁸ | X |
|---|---|---|---|---|---|---|
| H | H | H | H | CO₂CH₃ | H | O |
| H | H | H | H | CO₂CH₃ | CH₃ | O |
| H | H | H | H | CO₂CH₃ | CH₃ | CHF |
| H | H | H | H | CO₂C₂H₅ | CH₃ | CHF |
| H | H | H | H | CO₂C₂H₅ | H | CHF |
| H | H | H | H | CO₂(CH₂)₂CH₃ | CH₃ | CHF |
| H | H | H | H | CO₂(CH₂)₂CH₃ | H | CHF |
| H | H | H | H | CO₂(CH₂)₃CH₃ | CH₃ | CHF |
| H | H | H | H | CO₂(CH₂)₃CH₃ | H | CHF |
| H | H | H | H | CO₂CH₂C≡CH | CH₃ | CHF |
| H | H | H | Cl | CO₂CH₃ | CH₃ | CHF |
| H | H | H | Cl | CO₂C₂H₅ | CH₃ | CHF |
| H | H | H | Cl | CO₂(CH₂)₂CH₃ | CH₃ | CHF |
| H | H | H | Cl | CO₂(CH₂)₃CH₃ | CH₃ | CHF |
| H | H | H | Cl | CO₂CH₂C≡CH | CH₃ | CHF |
| H | H | F | Cl | CO₂CH₃ | CH₃ | CHF |
| H | H | F | Cl | CO₂C₂H₅ | CH₃ | CHF |
| H | H | F | Cl | CO₂(CH₂)₂CH₃ | CH₃ | CHF |
| H | H | F | Cl | CO₂(CH₂)₂CH₃ | H | CHF |
| H | H | F | Cl | CO₂CH₂CH= | CH₃ | CHF |
| H | H | F | Cl | CO₂CH(CH₃)C≡CH | CH₃ | CHF |
| H | H | F | Cl | CO₂CH₂CH=CH₂ | CH₃ | CHF |
| F | H | F | Cl | CO₂CH(CH₃)₂ | CH₃ | CH₂ |
| F | H | F | Cl | CO₂(CH₂)₃CH₃ | CH₃ | CH₂ |
| F | H | F | Cl | CO₂CH(CH₃)CH₂CH₃ | CH₃ | CH₂ |
| F | H | F | Cl | CO₂(CH₂)₂CH₃ | CH₃ | CH₂ |
| F | H | F | Cl | CO₂(CH₂)₃CH₃ | CH₃ | CH₂ |
| F | H | F | Cl | CO₂CH(CH₃)₂ | CH₃ | CH₂ |
| H | H | F | Cl | CO₂CH(CH₃)₂ | CH₃ | CHCl |

TABLE 7-continued

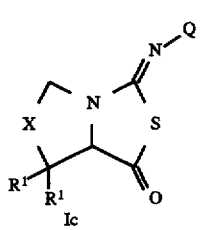 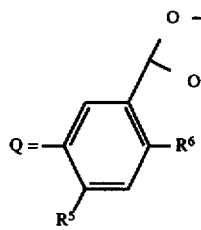

Ic

| R¹ | R¹ | R⁵ | R⁶ | R⁷ | R⁸ | X |
|---|---|---|---|---|---|---|
| H | H | F | Cl | CO₂(CH₂)₂CH₃ | CH₃ | CHCl |
| H | H | F | Cl | CO₂CH₃ | CH₃ | CHCl |
| H | H | F | Cl | CO₂CH₂CH₃ | CH₃ | CHCl |
| H | H | F | Cl | CO₂(CH₂)₃CH₃ | CH₃ | CHBr |
| H | H | F | Cl | CO₂(CH₂)₂CH₃ | CH₃ | CHBr |
| H | H | F | Cl | CO₂CH₃ | CH₃ | CHBr |
| H | H | F | Cl | CO₂CH₃ | CH₃ | CHOCHF₂ |
| H | H | F | Cl | CO₂CH₂CH₃ | CH₃ | CHOCHF₂ |
| H | H | F | Cl | CO₂(CH₂)₃CH₃ | CH₃ | CHOCHF₂ |
| H | H | F | Cl | CO₂CH₃ | CH₃ | CHOCF₃ |
| H | H | F | Cl | CO₂(CH₂)₃CH₃ | CH₃ | CHOCF₃ |
| H | H | F | Cl | CO₂CH₃ | CH₃ | CHOCH₂CF₃ |
| H | H | F | Cl | CO₂(CH₂)₃CH₃ | CH₃ | CHOCH₂CF₃ |
| F | H | H | H | CO₂CH₂C≡CH | CH₃ | CH₂ |
| F | H | H | Cl | CO₂CH₂C≡CH | CH₃ | CH₂ |
| F | H | F | Cl | CO₂CH₂C≡CH | CH₃ | CH₂ |
| F | H | F | Cl | CO₂CH(CH₃)C≡CH | CH₃ | CH₂ |
| H | H | F | Cl | CO₂CH₂CH=CH₂ | CH₃ | CHF |
| H | H | H | H | CO₂CH₂C≡CH | CH₃ | CHCl |
| H | H | H | Cl | CO₂CH₂C≡CH | CH₃ | CHCl |
| H | H | F | Cl | CO₂CH₂C≡CH | CH₃ | CHCl |
| H | H | F | Cl | CO₂CH(CH₃)C≡CH | CH₃ | CHCl |
| H | H | F | Cl | CO₂CH₂CH=CH₂ | CH₃ | CHCl |

TABLE 8

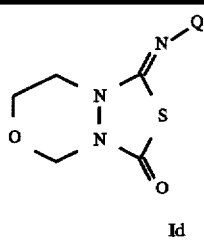 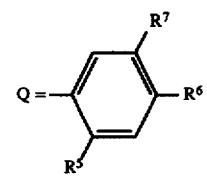

Id

| R⁵ | R⁶ | R⁷ |
|---|---|---|
| H | Cl | H |
| H | Br | H |
| H | CH₃ | H |
| F | Cl | H |
| Cl | Cl | H |
| F | Cl | OCH(CH₃)₂ |
| F | Cl | OCH₂C≡CH |
| F | Cl | OCH(CH₃)C≡CH |
| F | Cl | OCH₃ |
| F | Cl | OCH₂CH₂CH₃ |
| F | Cl | OCH₂CH=CH₂ |
| F | Cl | OCH₂CO₂CH₃ |
| F | Cl | OCH₂CO₂CH₂C≡CH |
| F | Cl | OCH₂CO₂C₅H₁₁ |

TABLE 8-continued

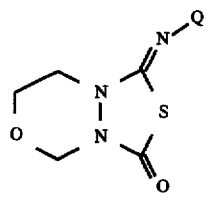 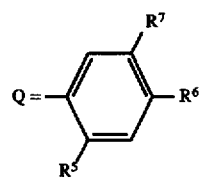

Id

| R⁵ | R⁶ | R⁷ |
|---|---|---|
| F | Cl | CN |
| F | Cl | SCH₃ |
| F | Cl | —O—CH₂CH=CHCO₂CH₃ |
| F | Cl | —O—CH₂—C₆H₅ |
| F | Cl | —O—CH₂—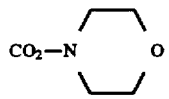 |
| F | Cl | SCH(CH₃)₂ |
| F | Cl | SCH₂CH=CH₂ |
| F | Cl | SCH₂C≡CH |
| F | Cl | SCH₂CO₂H |
| F | Cl | SCH₂CO₂CH₃ |
| F | Cl | OCH₂CON(CH₃)(CH₂CH₃) |
| F | Cl | OCH(CH₃)CH=N—OCH₃ |
| F | Cl | SCH₂CO₂CH₂C≡CH |
| F | Cl | OCHF₂ |
| F | Cl | OCH₂C(Cl)=CH₂ |
| F | Cl | OCF₂CHFCl |
| F | Cl | NHSO₂CH₃ |
| F | Cl | NHSO₂CH(CH₃)₂ |
| F | Cl | NHSO₂NHCH₃ |
| F | Cl | NHSO₂NHCH₂CH₃ |
| F | Cl | CO₂CH(CH₃)₂ |
| F | Cl | CO₂CH₂CH₂CH₃ |
| F | Cl | CO₂CH₂CF₃ |
| F | Cl | CON(CH₃)₂ |
| F | Cl | CO₂CH(CH₃)CH₂CH₃ |
| F | Cl | CO₂CH(CH₃)CF₃ |
| F | Cl | CO₂—N(CH₂CH₂)₂O |
| F | Cl | CO₂CH(CH₃)CH₂SCH₃ |
| Cl | Cl | H |
| Cl | Cl | OCHF₂ |
| Cl | Cl | OCH(CH₃)₂ |
| Cl | Cl | OCF₂CHFCl |
| Cl | Cl | OCH₂C≡CH |
| F | Cl | OCH₂P(O)(OC₂H₅)₂ |
| Cl | Cl | OCH(CH₃)C≡CH |
| Cl | Cl | OCH₂C(O)N(CH₃)₂ |
| F | Cl | O(CH₂)₂OCH₂CH₃ |
| Cl | Cl | SCH₂C≡CH |
| Cl | Cl | SCH₂CO₂H |
| Cl | Cl | SCH₂CO₂CH₂C≡CH |
| Cl | Cl | NHSO₂CH₃ |
| F | Cl | NHSO₂CF₃ |
| Cl | Cl | CO₂CH(CH₃)₂ |
| Cl | Cl | CO₂CH(CH₃)CH₂SCH₃ |
| Cl | Cl | CO₂CH(CH₃)CF₃ |
| Cl | Cl | CON(CH₃)₂ |

TABLE 8-continued

Structure Id: morpholine-N-N=C(S)-C(=O) with N-Q, where Q is phenyl with R⁵, R⁶, R⁷ substituents

| R⁵ | R⁶ | R⁷ |
|---|---|---|
| F | Cl | CO₂CH₂C≡CH |
| F | Cl | CO₂CH(CH₃)C≡CH |
| Cl | Cl | CO₂CH₂CF₃ |
| Cl | Cl | Cl |
| F | Cl | CO₂CH(CH₃)₂ |
| F | Cl | CO₂CH₃ |
| F | Cl | CO₂CH₂CH₃ |
| F | Cl | CO₂(CH₂)₂CH₃ |
| F | Cl | OCHF₂ |
| F | Cl | SCH₂CO₂H |
| F | Cl | SCH₂CO₂CH₃ |
| F | Cl | NHSO₂CH₂CH₃ |
| F | Cl | NHSO₂CH(CH₃)₂ |
| Cl | Cl | CO—N(morpholine) |
| Cl | Cl | CO₂(CH₂)₂CH₃ |
| F | Cl | CH=CHCO₂CH₂CH₃ |
| F | CN | CO₂CH(CH₃)₂ |
| Cl | CN | CO₂CH(CH₃)₂ |
| F | CN | OCH₂C≡CH |
| F | CN | OCH(CH₃)₂ |
| Cl | CN | OCH(CH₃)₂ |
| F | CN | CO₂CH₂CH₂CH₃ |
| Cl | CN | OCH₂C≡CH |
| F | CN | OCH(CH₃)C≡CH |
| F | CN | CO₂CH(CH₃)CH₂CH₃ |
| F | CN | OCHF₂ |
| F | CN | OCH(CH₃)₂ |
| F | CN | OCF₂CHF₂ |
| F | CN | SCH₂CO₂H |
| F | CN | NHSO₂CH₃ |
| F | CN | NHSO₂CF₃ |

TABLE 9

Structure Id: morpholine-fused thiadiazinone with N-Q; Q = phenyl with R⁵, R⁶ and CH₂C(R⁸)(R⁹)W group

| R⁵ | R⁶ | R⁸ | R⁹ | W |
|---|---|---|---|---|
| F | Cl | H | CH₃ | O |
| F | Cl | H | H | O |
| F | Cl | CH₃ | CH₃ | O |
| F | Cl | CH₃ | CH₂F | O |
| F | CN | CH₃ | CH₂F | O |
| F | Cl | H | CH₂CH₃ | O |

TABLE 9-continued

| R⁵ | R⁶ | R⁸ | R⁹ | W |
|---|---|---|---|---|
| F | Cl | H | CH₂F | O |
| F | Cl | H | CH₂Cl | O |
| F | Cl | H | CH₂Br | O |
| F | Br | H | CH₃ | O |
| F | CH₃ | H | CH₃ | O |
| F | OCH₃ | H | CH₃ | O |
| F | CN | H | CH₃ | O |
| F | CF₃ | H | CH₃ | O |
| F | OCF₂H | H | CH₃ | O |
| Cl | Cl | H | CH₃ | O |
| Cl | CN | H | CH₃ | O |
| F | CN | CH₃ | CH₃ | O |
| F | CN | H | CH₂F | O |
| F | CN | H | CH₂Cl | O |
| F | CN | H | CH₂Br | O |
| F | CN | H | CH(CH₃)₂ | O |
| F | CN | H | CH₂CH₂Cl | O |
| F | CN | H | CH₂CH₃ | O |
| F | CN | H | CH₂(CH₂)₂F | O |
| Cl | Br | H | CH₃ | O |
| Cl | CH₃ | H | CH₃ | O |
| Cl | OCH₃ | H | CH₃ | O |
| Cl | CN | H | CH₃ | O |
| Cl | CF₃ | H | CH₃ | O |
| Cl | OCF₂H | H | CH₃ | O |
| Cl | Cl | H | CH₂F | O |
| Cl | Cl | CH₃ | CH₂F | O |
| Cl | Cl | H | CH₂Cl | O |
| Cl | Cl | H | CH₂Br | O |
| Cl | Cl | H | CH₂CH₃ | O |
| Cl | Cl | CH₃ | CH₃ | O |

TABLE 10

Structure Id: morpholine-fused thiadiazinone with N-Q; Q = phenyl with R⁵, R⁶ and fused 5-membered ring bearing R⁸, R⁹, W

| R⁵ | R⁶ | R⁸ | R⁹ | W |
|---|---|---|---|---|
| H | H | H | Cl | S |
| F | Cl | H | Cl | S |
| Cl | Cl | H | Cl | S |
| F | Cl | H | CH₃ | S |
| F | Cl | H | CH₂CH₃ | S |
| H | SCH₃ | H | H | S |
| F | Cl | H | Cl | O |
| F | Cl | H | CH₃ | S |
| Cl | CN | H | Cl | S |
| Cl | Cl | H | CH₃ | S |
| Cl | Cl | H | CH₂CH₃ | S |
| Cl | Cl | H | Cl | O |
| F | CN | H | CH₃ | O |

TABLE 10-continued

| R⁵ | R⁶ | R⁸ | R⁹ | W |
|----|----|----|----|---|
| F  | CN | H  | CH₃ | S |
| Cl | Cl | H  | CH₃ | O |

TABLE 11

| R⁵ | R⁵ | W |
|----|----|---|
| F  | H | S |
| F  | CH₃ | S |
| F  | CH₂CH₃ | S |
| F  | CH₂C≡CH | S |
| Cl | CH₂C≡CH | S |
| F  | CH(CH₃)C≡CH | S |
| F  | CH₂C≡CH | O |
| Cl | H | S |
| Cl | CH₃ | S |
| Cl | CH₂CH₃ | S |
| Cl | CH₂C≡CH | S |
| F  | CH₂OCH₃ | S |
| F  | CH₂CH₂CH₃ | S |
| Cl | CH(CH₃)C≡CH | S |
| F  | CH(CH₃)₂ | S |
| F  | CH₂CH=CH₂ | S |
| Cl | CH₂CH=CH₂ | S |
| F  | CF₂CHF₂ | S |
| Cl | CH₂C≡CH | O |
| Cl | CH(CH₃)₂ | S |
| Cl | CH₂CH₂CH₃ | S |
| Cl | CF₂CHF₂ | S |
| F  | CH₂CH=CHCH₃ | S |

TABLE 12

| R⁵ | R⁸ | R⁹ | R¹⁰ | W |
|----|----|----|-----|---|
| H  | H  | H  | H | O |
| F  | H  | H  | CH₃ | O |
| F  | H  | H  | CH₂C≡CH | O |
| F  | H  | H  | CH(CH₃)C≡CH | O |
| Cl | H  | H  | CH₂C≡CH | O |
| F  | CH₃ | H | CH₂C≡CH | O |
| F  | H  | H  | CH₂C≡CH | S |
| Cl | H  | H  | CH₃ | O |
| F  | H  | H  | CH₂CH₃ | O |
| F  | H  | H  | CH₂CH₂CH₃ | O |
| F  | H  | H  | CH(CH₃)₂ | O |
| F  | H  | H  | CH₂CH=CH | O |
| Cl | H  | H  | CH(CH₃)C≡CH | O |
| Cl | H  | H  | CH₂C≡CH | S |
| F  | CH₃ | CH₃ | CH₂C≡CH | O |
| F  | H  | H  | H | O |
| Cl | H  | H  | CH₂CH₃ | O |
| Cl | H  | H  | CH(CH₃)₂ | O |
| Cl | CH₃ | H | CH₂CH=CH₂ | O |
| F  | CH₃ | H | CH₂C≡CH | O |
| Cl | CH₃ | CH₃ | CH₂C≡CH | O |
| Cl | CH₃ | CH₃ | CH₂CH=CH₂ | O |
| Cl | H  | H  | CH₂CH₂CH₃ | O |
| Cl | CH₃ | H | CH₂C≡CH | O |

TABLE 13

| R⁵ | R⁸ | R⁹ |
|----|----|----|
| H  | F  | F  |
| F  | F  | F  |
| F  | H  | H  |

TABLE 14

Id structure with R⁵, R⁶, R⁷, R⁸ substituents; Q group defined.

| R⁵ | R⁶ | R⁷ | R⁸ |
|----|----|----|----|
| H | H | CO$_2$CH$_3$ | H |
| H | H | CO$_2$CH$_3$ | CH$_3$ |
| H | H | CO$_2$C$_2$H$_5$ | CH$_3$ |
| H | H | CO$_2$C$_2$H$_5$ | H |
| H | H | CO$_2$(CH$_2$)$_2$CH$_3$ | CH$_3$ |
| H | H | CO$_2$(CH$_2$)$_2$CH$_3$ | H |
| H | H | CO$_2$CH$_2$C≡CH | CH$_3$ |
| H | Cl | CO$_2$CH$_3$ | CH$_3$ |
| H | Cl | CO$_2$C$_2$H$_5$ | CH$_3$ |
| H | Cl | CO$_2$(CH$_2$)$_2$CH$_3$ | CH$_3$ |
| H | Cl | CO$_2$(CH$_2$)$_2$CH$_3$ | CH$_3$ |
| H | Cl | CO$_2$CH$_2$C≡CH | CH$_3$ |
| F | Cl | CO$_2$CH$_3$ | CH$_3$ |
| F | Cl | CO$_2$C$_2$H$_5$ | CH$_3$ |
| F | Cl | CO$_2$(CH$_2$)$_2$CH$_3$ | CH$_3$ |
| F | Cl | CO$_2$(CH$_2$)$_2$CH$_3$ | H |
| F | Cl | CO$_2$CH$_2$C≡CH | CH$_3$ |
| F | Cl | CO$_2$CH(CH$_3$)C≡CH | CH$_3$ |
| F | Cl | CO$_2$CH$_2$CH=CH$_2$ | CH$_3$ |
| F | Cl | CO$_2$CH(CH$_3$)$_2$ | CH$_3$ |
| F | Cl | CO$_2$(CH$_2$)$_3$CH$_3$ | CH$_3$ |
| F | Cl | CO$_2$CH(CH$_3$)CH$_2$CH$_3$ | CH$_3$ |
| Cl | Cl | CO$_2$(CH$_2$)$_2$CH$_3$ | CH$_3$ |
| Cl | Cl | CO$_2$(CH$_2$)$_3$CH$_3$ | CH$_3$ |
| Cl | Cl | CO$_2$CH(CH$_3$)$_2$ | CH$_3$ |
| Cl | Cl | CO$_2$CH$_3$ | CH$_3$ |
| Cl | Cl | CO$_2$CH$_2$CH$_3$ | CH$_3$ |
| F | CN | CO$_2$(CH$_2$)$_3$CH$_3$ | CH$_3$ |
| Cl | Cl | CO$_2$(CH$_2$)$_2$CH$_3$ | H |
| F | CN | CO$_2$CH$_3$ | CH$_3$ |
| F | CN | CO$_2$CH$_2$CH$_3$ | CH$_3$ |
| Cl | CN | CO$_2$(CH$_2$)$_3$CH$_3$ | CH$_3$ |
| Cl | Cl | CO$_2$CH$_2$C≡CH | CH$_3$ |
| Cl | CN | CO$_2$CH$_2$C≡CH | CH$_3$ |
| Cl | CN | CO$_2$CH(CH$_3$)C≡CH | CH$_3$ |
| Cl | Cl | CO$_2$CH$_2$CH=CH$_2$ | CH$_3$ |
| Cl | Cl | CO$_2$CH(CH$_3$)C≡CH | CH$_3$ |

Formulations

Practical formulations of compounds of Formula I can be manufactured in a conventional manner, namely as powders, granules, pellets, solutions, suspensions, emulsions, wettable powders and emulsifiable concentrates, etc. Many of these formulations can be used directly. Sprayable preparations can be diluted with suitable media and sprayed in quantifies of a few to several hundred liters per hectare. Highly concentrated preparations are mainly used as intermediate products for further formulations. The formulations contain roughly between 0.1 and 99% by weight of active substance(s) and at least one carrier from the group a) 0.1 to 20% surfactant substances and b) about 1 to 99.9% solid or liquid diluents. More precisely, they contain these constituents in approximately the quantities stated below, where the formulations can be mixed with further active substances or additives.

|  | Weight-%* Active substance | Diluent | Surfactant |
|---|---|---|---|
| Wettable powders | 20–90 | 0–74 | 1–10 |
| Suspensions in oil, emulsions, solutions (including emulsifiable concentrates) | 3–50 | 40–95 | 0–15 |
| Aqueous suspensions | 10–50 | 40–84 | 1–20 |
| Dry powders | 1–25 | 70–99 | 0–5 |
| Granules and pellets | 0.1–95 | 5–99.9 | 0–15 |
| Highly concentrated preparations | 90–99 | 0–10 | 0–2 |

*Active substance plus a carrier comprising at least one surfactant and/or diluent = 100 weight-%.

Lower or higher active substance contents can of course be present, depending on the anticipated use and the physical properties of the compound. Higher quantity ratios of surfactant component to active substance are sometimes desirable and are attained by incorporation into the formulation or by mixing in the container.

Typical solid diluents are described in Watkins et al., Handbook of Insecticide Dust Diluents and Carriers, 2nd Ed., Dorland Books, Caldwell, New Jersey, though other mined or industrially prepared solid substances can also be used. The more absorbant diluents are preferred for wettable powders whilst the denser diluents are preferred for dry powders. Typical liquid diluents and solvents are described in Marsden, Solvents Guide, 2nd Ed., Interscience, New York, (1950) and are preferred for concentrated suspensions under 0.1%. Concentrated solutions are preferably resistant to phase separation at 0° C. Lists of surfactant substances and applications recommended for these are contained in McCutchen's Detergents and Emulsifiers Annual, MC Publishing. Corp., Ridgewood, N. J. and in Sisely and Wood, Encyclopedia of Surface Active Agents, Chemical Publishing Co. Inc., New York, (1964). All formulations may contain small quantities of additives for reducing frothing, agglomeration, corrosion and growth of microorganisms etc.

The methods for preparation of such products are well known. Solutions are prepared by simply mixing the ingredients. Finely powdered solid preparations are obtained by mixing and, usually, by grinding, for example in a hammer mill or jet mill. Suspensions axe obtained by wet grinding (see for example Littler, U.S. Pat. No. 3,060,084). Granules and pellets can be prepared by spraying the active substance onto preformed granular carriers or by agglomerating them. For these see J. E Browning, Agglomeration, Chemical Engineering, Dec. 4, (1967), p 147 ff. and Perry's Chemical Engineer's Handbook, 5th Ed., McGraw-Hill, New York, (1973), pp 8–57 ff.

For further information on formulation technology see for example:

H. M. Loux, U.S. Pat. No. 3,235,361, 15 Feb. 1966, column 6, line 16 to column 7, line 19 and Examples 10 to 41;

R. W. Luckenbaugh, U.S. Pat. No. 3,309,192, 14 Mar. 1967, column 5, line 43 to column 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, 23 Jun. 1959, column 3, line 66 to column 5, line 17 and Examples 1–4;

G. C. Klingman, Weed Control as a Science, John Wiley and Sons, Inc., New York, (1961), pp 81–96 and J. D. Fryer and S. A. Evans, *Weed Control Handbook*, 5th Ed., Blackwell Scientific Publications, Oxford, (1968), pp 101–103.

Unless stated otherwise, the figures given in the following Examples are parts by weight.

EXAMPLE A

| Wettable powder | |
|---|---|
| 1-[(2,4-Dichlorophenyl)imino]dihydro-1H,3H,5H-[1,3,4]thiadiazolo[3,4-c]-[1,3,4]oxadiazin-3-one | 80% |
| Sodium alkylnaphthalenesulfonate | 2% |
| Sodium ligninsulfonate | 2% |
| Synthetic amorphous silicic acid | 3% |
| Kaolinite | 13% |

The ingredients are mixed together and ground in a hammer mill until all the solids essentially have a particle size of less than 50 µm, after which they are mixed again and packed.

EXAMPLE B

| Wettable powder | |
|---|---|
| 1-[(2,4-Dichlorophenyl)imino]dihydro-1H,3H,5H-[1,3,4]thiadiazolo[3,4-c]-[1,3,4]oxadiazin-3-one | 50% |
| Sodium alkylnaphthalenesulfonate | 2% |
| Low-viscosity methylcellulose | 2% |
| Diatomic earth | 46% |

The ingredients are mixed, coarsely ground in a hammer mill and then ground in a jet mill so that practically all particles have a diameter of less than 10 µm. The product is then mixed again before packing.

EXAMPLE C

| Granulate | |
|---|---|
| Wettable powder of Example B | 5% |
| Attapulgite granulate (USS 20–40 mesh; 0.84–0.42 mm) | 95% |

A slurry of wettable powder with 25 % solid substances is sprayed into a double cone mixer and the granules are then dried and packed.

EXAMPLE D

| Extrusion-pressed pellets | |
|---|---|
| 1-[(2,4-Dichlorophenyl)imino]dihydro-1H,3H,5H-[1,3,4]thiadiazolo[3,4-c]-[1,3,4]oxadiazin-3-one | 25% |
| Anhydrous sodium sulfate | 10% |
| Crude calcium ligninsulfonate | 5% |
| Sodium alkylnaphthalenesulfonate | 1% |
| Calcium/magnesium bentonite | 59% |

The ingredients are mixed together, ground in a hammer mill and then moistened with about 12% water. The mixture is extrusion-pressed into cylinders with a diameter of about 3 mm which are then cut up into pellets of a length of about 3 mm. These can be used directly after drying; however, the dried pellets can be ground up so that the ground particles pass through a USS No. 20 sieve (mesh diameter 0.84 mm). The granules remaining on a sieve of USS No. 40 (mesh diameter 0.42 mm) can be packed for use, whilst the fine particles are recycled.

EXAMPLE E

| Granulate of low tensile strength | |
|---|---|
| 1-[(2,4-Dichlorophenyl)imino]dihydro-1H,3H,5H-[1,3,4]thiadiazolo[3,4-c]-[1,3,4]oxadiazin-3-one | 1% |
| N,N-Dimethylformamide | 9% |
| Attapulgite granulate (USS sieves 20 to 40) | 90% |

The active substance is dissolved in the solvent and the solution is sprayed on to dust-free granules in a double-cone mixer. After spraying of the solution the mixer is left running for a further short time, after which the granules are packed.

EXAMPLE F

| Granulate | |
|---|---|
| 1-[(2,4-Dichlorophenyl)imino]dihydro-1H,3H,5H-[1,3,4]thiadiazolo[3,4-c]-[1,3,4]oxadiazin-3-one | 80% |
| Wetting agent | 1% |
| Crude ligninsulfonate (with 5–20% of the natural sugars) | 10% |
| Attapulgite clay | 9% |

The ingredients are mixed and ground until they pass through a 100-mesh sieve. This material is then put in a fluid bed granulator, where the airflow is adusted so that the material is easily whirled up and a free water jet is sprayed on to the whirled up material. Fluidisation and spraying are continued until granules of the desired size are obtained. Spraying is then stopped, but fluidisation is continued, optionally with heating, until the water content has fallen to the desired level, which is generally below 1%. The material is then drawn off and the desired granule size range (usually 1410 to 149 µm) is obtained by sieving on 14- to 100-mesh sieves, after which the granules are packed for use.

EXAMPLE G

| Aqueous suspension | |
|---|---|
| 1-[(2,4-Dichlorophenyl)imino]dihydro-1H,3H,5H-[1,3,4]thiadiazolo[3,4-c]-[1,3,4]oxadiazin-3-one | 40.0% |
| Polyacrylic acid-based thickener | 0.3% |
| Dodecylphenol polyethylene glycol ether | 0.5% |
| Disodium phosphate | 1.0% |
| Monosodium phosphate | 0.5% |
| Polyvinyl alcohol | 1.0% |
| Water | 56.7% |

The ingredients are mixed and ground together in a sand mill to obtain particles essentially of a size of less than 5 µm.

EXAMPLE H

| Strong concentrate | |
|---|---|
| 1-[(2,4-Dichlorophenyl)imino]dihydro-1H,3H,5H-[1,3,4]thiadiazolo[3,4-c]-[1,3,4]oxadiazin-3-one | 99.0% |
| Silicic acid-Aerogel | 0.5% |
| Synthetic amorphous silicic acid | 0.5% |

The ingredients are mixed and ground in a hammer mill to obtain material that passes through a USS sieve No. 50 (0.3 mm aperture). The concentrate may if necessary also contain further ingredients.

EXAMPLE I

| Wettable powder | |
|---|---|
| 1-[(2,4-Dichlorophenyl)imino]dihydro-1H,3H,5H-[1,3,4]thiadiazolo[3,4-c]-[1,3,4]oxadiazin-3-one | 90.0% |
| Dioctylsodium sulphosuccinate | 0.1% |
| Synthetic fine silicic acid | 9.9% |

The ingredients are mixed and ground in a hammer mill to obtain particles essentially of a size of less than 100 μm. The material is sieved through a USS No. 50 sieve and then packed.

EXAMPLE J

| Wettable powder | |
|---|---|
| 1-[(2,4-Dichlorophenyl)imino]dihydro-1H,3H,5H-[1,3,4]thiadiazolo[3,4-c]-[1,3,4]oxadiazin-3-one | 40% |
| Sodium ligninsulfonate | 20% |
| Montmorillonite clay | 40% |

The ingredients are thoroughly mixed, coarsely ground in a hammer mill, then ground in an air-jet mill to obtain particles essentially of a size of less than 10 μm and then mixed again and packed.

EXAMPLE K

| Suspension in oil | |
|---|---|
| 1-[(2,4-Dichlorophenyl)imino]dihydro-1H,3H,5H-[1,3,4]thiadiazolo[3,4-c]-[1,3,4]oxadiazin-3-one | 35% |
| Mixture of polyalcohol carboxylic acid esters and oil-soluble petroleum sulfonates | 6% |
| Xylene | 59% |

The ingredients are mixed and ground in a sand mill to obtain particles essentially of a size of less than 5 μm. The product can be used as it is or diluted with oil or emulsified in water.

EXAMPLE L

| Fine powder | |
|---|---|
| 1-[(2,4-Dichlorophenyl)imino]dihydro-1H,3H,5H-[1,3,4]thiadiazolo[3,4-c]-[1,3,4]oxadiazin-3-one | 10% |

| Fine powder | |
|---|---|
| Attapulgite | 10% |
| Pyrophyllite | 80% |

The active substance is mixed with attapulgite and then passed through a hammer mill to obtain particles of essentially less than 200 μm in diameter. The ground concentrate is then mixed with the powdered pyrophyllite until a homogeneous mixture is obtained.

EXAMPLE M

| Suspension in oil | |
|---|---|
| 1-[(2,4-Dichlorophenyl)imino]dihydro-1H,3H,5H-[1,3,4]thiadiazolo[3,4-c]-[1,3,4]oxadiazin-3-one | 25% |
| Polyoxyethylene sorbitol hexaoleate | 5% |
| High molecular weight aliphatic hydrocarbon oil | 70% |

The ingredients are ground together in a sand mill until the size of the solid particles is below about 5 μm. The resultant thick suspension can be used as it is, though it is preferably used after dilution with oils or after emulsification in water.

Application

The compounds of the invention are active weedkillers. They are used for wide-range weed control in the pre- and/or post-germination period in areas in which complete control of all vegetation is desirable, such as, for example, around industrial plants, warehouses, car parks, reclaimed land, fenced areas, roads and railway lines. Some of these compounds are used for selective weed control in crops such as rice, wheat, oats, maize, soybeans, sugar-beet, cotton and groundnuts. The compounds of the invention are active weedkillers for selective and/or general weed control of dicotyledonous weeds and grasses in all plantation crops, including coffee, cocoa, sugar cane, oil palms, rubber, citrus fruits, grapes, fruit trees, nut trees, bananas, plantain, pineapples and conifers such as Scots and other pines and spruces.

The compounds can be used in the pre- and/or post-germination period using techniques such as 'banding', direct spraying or broadcast sowing. The applied quantities are determined by a number of factors, including whether they are used as general herbicides, the environment in which they are used, the crop being treated, the types of weeds to be controlled, the weather at the time and the climate in general, the choice of formulation, the method of application, foliage stage, and the like. The quantity of the compounds of the invention that appears optimum to the expert can thus be selected for use in areas where complete control of the entire vegetation is desirable, such as, for example, around storage tanks, industrial plants, advertising areas, roads; railway lines, and fencing. Alternatively, when the correct quantities have been selected for application, the compounds of the invention can be used for selective weed control in plantations for groundnuts, citrus fruits, sugar cane, coffee, oil palms, rubber, cocoa, grapes, fruit trees, nut trees, pineapples and bananas. The compounds in question are generally applied in quantities of between 0.001 to 20 kg/hectare, the preferred application quantity being 0.01 to 2 kg/hectare.

The compounds of the invention can be used in combination with other herbicides which are listed below. They are particularly useful in combination with triazines, triazoles, uracils, ureas, amides, carbamates, bipyridyl and phenoxy compounds, sulphone ureas and imidazoles for total control of vegetation in plantation and other crops. The compounds can also be used in combination with mefluidide, glyphosate or gluphosinate.

A mixture of one or more of the following herbicides with a compound of the invention can be particularly useful for weed control. Examples of other herbicides with which the compounds of the invention can be formulated are: .

Acetochlor, acifluorfen, acrolein, 2-propenal, alachlor, ametryn, amidosulfuron, ammonium sulfamate, amitroles, Anilofos, asulam, atrazines, Barban, Benefin, bensulfuron methyl, bensulides, bentazone, benzofluorine, Benzoylprop, Bifenox, bromacil, bromoxynil, bromoxynil heptanoate and octanoate, butachlor, buthidazoles, butraline, butylates, cacodylic acid, 2-chloro-N,N-di-2-propenyl-acetamide, 2-chloroallyldiethyldithiocarbamate, Chloramben, chlorbromuron, chloridazon, chlorimuron ethyl, chlormethoxynil, chlomitrofen, chloroxuron, chlorpropham, chlorsulfuron, chlortoluron, cinmethylin, cinosulfuron, Clethodium, clomazone, cloproxydim, clopyralid, methylarsonic acid or the corresponding calcium salt, cyanazines, cycloates, cyluron, Cyperquat, cyprazines, cyprazoles, cypromid, Delapon, dazomate, dimethyl 2,3,5,6-tetrachloro-1,4-dibenzenedicarboxylate, Desmedipham, Desmetryn, Dicamba, dichlobenil, dichlorprop, Diclofop, diethatyl, Difenzoquat, diflufenican, dimepiperates, dinitramines, Dinoseb, diphenamid, Dipropetryn, Diquat, diuron, 2-methyl-4,6-dinitrophenol, methylarsonic acid disodium salt, Dymron, Endothall, S-ethyldipropylcarbamothioate, Esprocarb, ethalfluralin, ethametsulfuron methyl, ethofumesate, Fenac, Fenoxaprop, fenuron, fenuron trichloroacetate, Flameprop, Fluazifop, Fluazifop-P, fluchloralin, Flumesulam, Flumipropyn, fluometuron, fluorochloridone, fluorodifen, fluoroglycofen, flupoxam, fluridones, Fluroxypyr, fluzasulfuron, Fomasafen, fosamines, glyphosates, Haloxyfop, hexaflurates, hexazinones, imazamethabenz, Imazethapyr, imazosulfuron, Ioxynil, isopropalin, isoproturon, isottron, isoxaben, karbutilate, lactofen, Lenacil, linuron, metobenzuron, metsulfuron methyl, methylarsonic acid, monoammonium methylarsonate, (4-chloro-2-methylphenoxy)acetic acid, S,S'-dimethyl-2-(difluoromethyl))-4-(2-methylpropyl)-6-(trifluoromethyl)-3,5-pyridinedicarbothioate, Mecoprop, Mefenacet, mefluidides, methalpropalin, methabenzthiazttron, Metham, methazoles, methoxuron, Metolachlor, Metribuzin, 1,2-dihydropyridazine-3,6-dione, molinates, monolinuron, monuron, monuron trichloroacetate, monososodium methylarsonate, napropamides, naptalam, neburon, nicosulfuron, nitralin, nitrofen, nitrofluorofen, Norea, norflurazon, oryzalin, oxadiazon, oxyflorofen, Paraquat, pebulates, pendimethalin, perfluidone, phenmedipham, picloram, 5-[2-chloro-4-(trifluoromethyl)phenoxy]-2-nitroacetophenone oxime-O-acetic acid methyl ester, pretilachlor, primisulfuron, procyazines, profluralin, prometon, Prometryn, pronamides, propachlor, propanil, propazines, Propham, prosulfalin, Prynachlor, pyrazolates, pyrazon, pyrazosulfuron ethyl, Quinchlorac, Quizalofop ethyl, rimsulfuron, secbumeton, sethoxydim, siduron, simazines, 1-(α,α-dimethylbenzyl)-3-(4-methylphenyl)urea, sulfometuron methyl, trichloroacetic acid, tebuthiuron, terbacil, terbuchlor, terbuthylazines, terbutol, Terbutryn, thifensulfuron methyl, thiobencarb, triallates, trialkoxydim, triasulfuron, tribenuron methyl, triclopyr, tridiphans, trifluralin, trimeturon, (2,4-dichlorophenoxy)acetic acid, 4-(2,4-dichlorophenoxy)butyric acid, vemolates and xylachlor. Results for Tests A–D are given in Tables A–D.

INDEX TABLE A

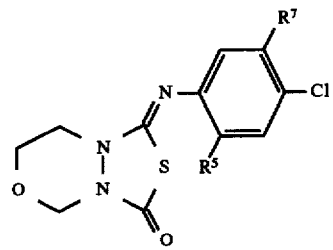

| Cmpd # | R$^5$ | R$^7$ | mp° |
|---|---|---|---|
| 1 | H | H | oil |
| 2 | Cl | H | oil |
| 3 | Cl | Cl | oil |
| 9 | F | CO$_2$CH(CH$_3$)$_2$ | 118–119° C. |
| 10 | f | OCH2CH=CH2 | 119° C. |
| 11 | F | OCH$_2$C≡CH | 194° C. |
| 12 | F | OCH$_2$-cyclopropyl | 104° C. |
| 13 | F | OCH(CH$_3$)C≡CH | 108° C. |
| 14 | F | OCH(CH$_3$)$_2$ | 129° C. |
| 15 | F | OCH$_2$Ph | 126° F. |
| 16 | F | OCH$_2$CH=CHCO$_2$CH$_3$ | 119–121° C. |

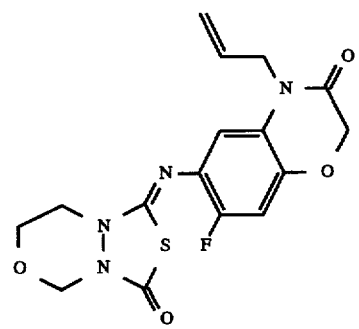

Compound 4: mp 151° C.

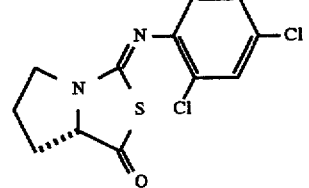

Compound 5: oil

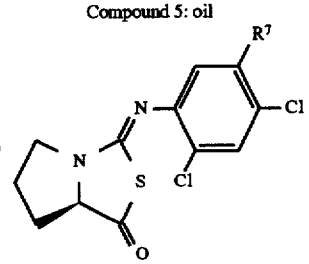

Compound 6: R$^7$=Cl, oil
Compound 7: R$^7$=H, oil

INDEX TABLE A-continued

[Structure: morpholine-linked thiadiazine with N=C connected to phenyl bearing R7 and Cl, with R5 substituent]

| Cmpd # | R5 | R7 | mp |
|--------|----|----|-----|

[Structure of Compound 8: pyrrolidine with Cl substituent, connected via N=C-S to a fused bicyclic system containing N-allyl amide and oxazine with F substituent]

Compound 8: mp 162° C.
[a] ¹H NMR data for oils are given in Index Table B.

INDEX TABLE B

| Cmpd No. | ¹H NMR Data[a] | |
|----------|----------------|---|
| 1 | Me₂SO-d₆ | 4.11(t,2H), 4.50(t,2H), 5.18(s,2H), 6.98 (d,2H), 7.37(d,2H). |
| 2 | Me₂SO-d₆ | Two isomers: 3.82 and 4.01(2t,2H), 4.12 and 4.53(2t,2H), 5.17 and 5.22(2s,2H), 7.10(2d,1H), 7.30–7.35(m,1H), 7.50 and 7.56(2d,1H). |
| 3 | CDCl₃ | 3.85(t,2H), 4.05(t,2H), 5.16(s,2H), 7.07 (s,1H), 7.53(s,1H). |
| 5 | CDCl₃ | 1.85–1.98(m,1H), 2.08–2.22(m,1h), 2.22–2.37(m,2H), 3.55–3.65(m,1H), |

INDEX TABLE B

| Cmpd No. | ¹H NMR Data[a] | |
|----------|----------------|---|
|  |  | 4.00–4.11(m,1H), 4.54(dd,1H), 6.84 (d,1H), 7.17(d,1H), 7.40(s,1H). |
| 6 | CDCl₃ | 1.85–1.95(m,1H), 2.08–2.19(m,1H), 2.20–2.35(m,2H), 3.51–3.61(m,1H), 3.95–4.08(m,1H), 4.52(dd,1H), 7.01 (s,1H), 7.43(s,1H). |
| 7 | CDCl₃ | 1.85–1.98(m,1H), 2.08–2.22(m,1h), 2.22–2.37(m,2H), 3.55–3.65(m,1H), 4.00–4.11(m,1H), 4.54(dd,1H), 6.84 (d,1H), 7.17(d,1H), 7.40(s,1H). |

[a] ¹H NMR data are in ppm downfield from tetramethylsilane and were measured at 500 MHz. Couplings are designated by s-singlet, d-doublet, t-triplet, m-multiplet, dd-doublet of doublets.

TEST A

Seeds of barley (*Hordeum vulgare*), barnyardgrass (*Echinochloa crus-galli*), bedstraw (*Galium aparine* ), blackgrass (*Alopecurus myosur oides* ), cheatgrass (*Bromus secalinus*), chickweed (*Stellaria media*), cocklebur (*Xanthium pensylvanicum*), corn (*Zea mays*), cotton (*Gossypium hirsutum*), crabgrass (Digitaria spp.), downy brome (*Bromus tectorum*), giant foxtail (*Setaria faberii*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| | COMPOUND | | | | | | COMPOUND | | | | |
|---|---|---|---|---|---|---|---|---|---|---|---|
| Rate 1000 g/ha | 2 | 3 | 5 | 6 | 7 | Rate 1000 g/ha | 2 | 3 | 5 | 6 | 7 |
| Postemergence | | | | | | Preemergence | | | | | |
| Barley | 3 | 2 | 2 | 2 | 3 | Barley | 0 | 0 | 0 | 0 | 0 |
| Barnyardgrass | 8 | 4 | 4 | 4 | 5 | Barnyardgrass | 7 | 0 | 0 | 0 | 0 |
| Bedstraw | 7 | 5 | 5 | 6 | 3 | Bedstraw | 7 | 0 | 2 | 0 | — |
| Blackgrass | 2 | 2 | 2 | 1 | 2 | Blackgrass | 1 | 0 | 0 | 0 | 0 |
| Cheatgrass | — | — | — | — | — | Cheatgrass | — | — | — | — | — |
| Chickweed | 2 | 2 | 1 | 0 | 0 | Chickweed | 0 | 0 | 2 | 0 | 0 |
| Cocklebur | 7 | 4 | 5 | 6 | 6 | Cocklebur | 0 | 0 | 0 | 0 | 0 |
| Corn | 3 | 3 | 2 | 2 | 3 | Corn | 3 | 0 | 0 | 0 | 0 |
| Cotton | 10 | 9 | 10 | 9 | 9 | Cotton | 2 | 2 | 0 | 0 | 0 |
| Crabgrass | 5 | 3 | 3 | 3 | 4 | Crabgrass | 8 | 3 | 0 | 0 | 0 |
| Downy brome | 3 | 0 | 3 | 1 | 1 | Downy brome | 1 | 0 | 0 | 0 | 0 |
| Giant foxtail | 5 | 2 | 3 | 4 | 3 | Giant foxtail | 7 | 3 | 0 | 0 | 0 |
| Morningglory | 8 | 7 | 6 | 9 | 8 | Morningglory | 0 | 0 | 0 | 0 | 0 |
| Nutsedge | 7 | — | 0 | 0 | 6 | Nutsedge | 0 | 8 | 0 | 0 | 0 |
| Rape | 8 | 5 | 9 | 5 | 3 | Rape | 10 | 8 | 0 | 0 | 0 |
| Rice | 3 | 3 | 3 | 0 | 2 | Rice | 0 | 0 | 0 | 0 | 0 |
| Sorghum | 4 | 3 | 4 | 3 | 4 | Sorghum | 2 | 0 | 0 | 0 | 0 |
| Soybean | 8 | 3 | 4 | 3 | 6 | Soybean | 0 | 0 | 0 | 0 | 0 |

TABLE A-continued

| | | | | | | | | | | | | | | | | |
|---|---|---|---|---|---|---|---|---|---|---|---|---|---|---|---|---|
| Sugarbeet | 9 | 6 | 8 | 10 | 9 | Sugarbeet | 4 | 2 | 0 | 0 | 0 | | | | | |
| Velvetleaf | 10 | 9 | 8 | 9 | 10 | Velvetleaf | 10 | 10 | 0 | 0 | 0 | | | | | |
| Wheat | 3 | 1 | 2 | 1 | 2 | Wheat | 0 | 0 | 0 | 0 | 0 | | | | | |
| Wild buckwheat | 9 | 8 | 10 | 10 | 9 | Wild buckwheat | 9 | 2 | 0 | 0 | 0 | | | | | |
| Wild oat | 2 | 0 | 2 | 2 | 2 | Wild oat | 3 | 0 | 0 | 0 | 0 | | | | | |

| | COMPOUND | | | | | | | | | | | | | | | |
|---|---|---|---|---|---|---|---|---|---|---|---|---|---|---|---|---|
| Rate 200 g/ha | 1 | 2 | 3 | 4 | 5 | 6 | 7 | 8 | 9 | 10 | 11 | 12 | 13 | 14 | 15 | 16 |
| Postemergence | | | | | | | | | | | | | | | | |
| Barley | 3 | 3 | 0 | 5 | 2 | 2 | 2 | 5 | 8 | 7 | 9 | 7 | 8 | 8 | 3 | 9 |
| Barnyardgrass | 5 | 5 | 3 | 9 | 2 | 2 | 3 | 7 | 10 | 9 | 9 | 9 | 10 | 10 | 5 | 9 |
| Bedstraw | 5 | 6 | 5 | 10 | 3 | 3 | 3 | 10 | 10 | 10 | 10 | 9 | 10 | 10 | 9 | 10 |
| Blackgrass | 2 | 1 | 0 | 7 | 2 | 1 | 1 | 4 | 9 | 8 | 9 | 8 | 9 | 8 | 4 | 4 |
| Cheatgrass | — | — | — | — | — | — | — | — | — | — | — | — | 9 | 8 | 3 | 4 |
| Chickweed | 2 | 1 | 0 | 10 | 0 | 0 | 0 | 10 | 10 | 10 | 10 | 8 | 10 | 8 | 7 | 6 |
| Cocklebur | 6 | 6 | 5 | 10 | 6 | 5 | 5 | 10 | 10 | 10 | 10 | 10 | 10 | 10 | 10 | 10 |
| Corn | 3 | 3 | 2 | 7 | 2 | 2 | 2 | 2 | 8 | 8 | 9 | 8 | 8 | 9 | 2 | 4 |
| Cotton | 9 | 10 | 9 | 10 | 9 | 8 | 9 | 10 | 10 | 10 | 10 | 10 | 10 | 10 | 10 | 10 |
| Crabgrass | 5 | 2 | 3 | — | 2 | 3 | 2 | 7 | 8 | 9 | 9 | 9 | 9 | 9 | 7 | 4 |
| Downy brome | 3 | 3 | 1 | 5 | 1 | 0 | 0 | 4 | 6 | 8 | 8 | 6 | — | — | — | — |
| Giant foxtail | 4 | 4 | 3 | 9 | 2 | 1 | 2 | 6 | 8 | 9 | 9 | 9 | 9 | 9 | 6 | 6 |
| Morningglory | 8 | 7 | 6 | 10 | 5 | 6 | 7 | 10 | 10 | 10 | 10 | 10 | 10 | 10 | 10 | 9 |
| Nutsedge | 2 | — | 6 | 5 | 0 | 4 | 0 | 0 | 4 | 6 | 7 | 3 | 4 | 7 | 1 | 1 |
| Rape | 2 | 7 | 4 | 10 | 4 | 2 | 1 | 10 | 10 | 10 | 10 | 10 | 10 | 10 | 10 | 10 |
| Rice | 3 | 2 | 2 | 9 | 1 | 0 | 0 | 4 | 10 | 9 | 9 | 9 | 10 | 9 | 4 | 4 |
| Sorghum | 4 | 3 | 2 | 8 | 3 | 3 | 3 | 6 | 9 | 9 | 9 | 9 | 9 | 9 | 4 | 7 |
| Soybean | 5 | 3 | 3 | 10 | 3 | 3 | 3 | 10 | 9 | 9 | 10 | 9 | 10 | 10 | 8 | 9 |
| Sugarbeet | 3 | 4 | 3 | 10 | 5 | 6 | 7 | 10 | 10 | 10 | 10 | 10 | 10 | 10 | 10 | 10 |
| Velvetleaf | 9 | 9 | 9 | 10 | 8 | 7 | 6 | 10 | 10 | 10 | 10 | 10 | 10 | 10 | 10 | 10 |
| Wheat | 1 | 1 | 0 | 7 | 0 | 0 | 1 | 5 | 6 | 8 | 9 | 8 | 9 | 9 | 4 | 9 |
| Wild buckwheat | 6 | 8 | 9 | 10 | 7 | 8 | 7 | 10 | 10 | 10 | 10 | 10 | 10 | 10 | 10 | 10 |
| Wild oat | 2 | 2 | 0 | 7 | 1 | 0 | 1 | 5 | 7 | 8 | 9 | 7 | 9 | 8 | 3 | 8 |
| Preemergence | | | | | | | | | | | | | | | | |
| Barley | 0 | 0 | 0 | 6 | 0 | 0 | 0 | 0 | 6 | 5 | 6 | 2 | 6 | 2 | 0 | 1 |
| Barnyardgrass | 0 | 0 | 0 | 8 | 0 | 0 | 0 | 0 | 9 | 9 | 9 | 9 | 9 | 10 | 3 | 6 |
| Bedstraw | 0 | 2 | 0 | 10 | — | — | 0 | 3 | 10 | 10 | 10 | 10 | 10 | 10 | 10 | 10 |
| Blackgrass | 0 | 0 | 0 | 6 | 0 | 0 | 0 | 7 | 7 | 4 | 6 | 4 | 7 | 8 | 3 | 1 |
| Cheatgrass | — | — | — | — | — | — | — | — | — | — | — | — | 6 | 8 | 3 | 1 |
| Chickweed | 0 | 0 | 0 | 10 | 0 | 0 | 0 | 10 | 10 | 10 | 10 | 10 | 10 | 9 | 6 | 0 |
| Cocklebur | 0 | 0 | 0 | 10 | 0 | 0 | 0 | 3 | 10 | 10 | 10 | 9 | 10 | 9 | 8 | 8 |
| Corn | 0 | 0 | 0 | 4 | 0 | 0 | 0 | 0 | 6 | 7 | 8 | 2 | 6 | 6 | 2 | 1 |
| Cotton | 0 | 0 | 0 | 8 | 0 | 0 | 0 | 9 | 10 | 10 | 10 | 10 | 10 | 10 | 7 | 10 |
| Crabgrass | 4 | 3 | 2 | 9 | 0 | 0 | 0 | 9 | 10 | 10 | 9 | 10 | 10 | 10 | 8 | 4 |
| Downy brome | 0 | 0 | 0 | 3 | 0 | 0 | 0 | 0 | 5 | 6 | 7 | 6 | — | — | — | — |
| Giant foxtail | 0 | 2 | 0 | 9 | 0 | 0 | 0 | 0 | 10 | 10 | 10 | 8 | 9 | 10 | 5 | 3 |
| Morningglory | 0 | 0 | 0 | 10 | 0 | 0 | 0 | 10 | 10 | 10 | 10 | 10 | 10 | 10 | 10 | 7 |
| Nutsedge | — | 0 | 0 | 0 | 0 | — | 0 | — | — | 10 | 7 | 9 | 4 | 7 | 9 | 8 |
| Rape | 0 | 2 | 0 | 10 | 0 | 0 | 0 | 9 | 10 | 10 | 10 | 10 | 10 | 10 | 8 | 10 |
| Rice | 0 | 0 | 0 | 3 | 0 | 0 | 0 | 0 | 6 | 7 | 8 | 3 | 9 | 9 | 0 | 3 |
| Sorghum | 0 | 0 | 0 | 3 | 0 | 0 | 0 | 4 | 6 | 7 | 5 | 9 | 9 | 9 | 0 | 2 |
| Soybean | 0 | 0 | 0 | 10 | 0 | 0 | 0 | 8 | 10 | 10 | 10 | 10 | 10 | 10 | 2 | 2 |
| Sugarbeet | 0 | 0 | 0 | 10 | 0 | 0 | 0 | 9 | 10 | 10 | 10 | 10 | 10 | 10 | 10 | 10 |
| Velvetleaf | 10 | 8 | 7 | 10 | 0 | 0 | 0 | 10 | 10 | 10 | 10 | 10 | 10 | 10 | 10 | 10 |
| Wheat | 0 | 0 | 0 | 7 | 0 | 0 | 0 | 2 | 6 | 3 | 7 | 3 | 7 | 6 | 1 | 2 |
| Wild buckwheat | 0 | 0 | 1 | 10 | 0 | 0 | 0 | 2 | 10 | 10 | 10 | 10 | 10 | 10 | 7 | 6 |
| Wild oat | 0 | 0 | 0 | 8 | 0 | 0 | 0 | 4 | 7 | 7 | 9 | 6 | 9 | 8 | 3 | 0 |

| | COMPOUND | | | | | | | | | |
|---|---|---|---|---|---|---|---|---|---|---|
| Rate 50 g/ha | 1 | 4 | 8 | 9 | 10 | 11 | 12 | 13 | 14 | 15 | 16 |
| Postemergence | | | | | | | | | | | |
| Barley | 2 | 4 | 4 | 5 | 6 | 7 | 4 | 6 | 4 | 5 | 5 |
| Barnyardgrass | 3 | 6 | 6 | 8 | 9 | 9 | 9 | 9 | 9 | 4 | 9 |
| Bedstraw | 3 | 10 | 10 | 10 | 10 | 10 | 9 | 10 | 10 | 8 | 9 |
| Blackgrass | 1 | 3 | 4 | 6 | 6 | 8 | 4 | 7 | 6 | 3 | 3 |
| Cheatgrass | — | — | — | — | — | — | — | 7 | 4 | 3 | 3 |
| Chickweed | 2 | 10 | 10 | 9 | 8 | 10 | 7 | 9 | 4 | 4 | 6 |
| Cocklebur | 6 | 10 | 10 | 10 | 10 | 10 | 10 | 10 | 9 | 9 | 10 |
| Corn | 3 | 5 | 3 | 5 | 6 | 8 | 5 | 5 | 5 | 2 | 3 |
| Cotton | 9 | 10 | 10 | 10 | 10 | 10 | 10 | 10 | 10 | 10 | 10 |
| Crabgrass | 3 | 5 | 6 | 6 | 8 | 9 | 8 | 8 | 8 | 7 | 6 |
| Downy brome | 3 | 4 | 4 | 5 | 4 | 6 | 4 | — | — | — | — |
| Giant foxtail | 3 | 6 | 6 | 6 | 7 | 9 | 8 | 7 | 8 | 5 | 8 |

TABLE A-continued

| | | | | | | | | | | | |
|---|---|---|---|---|---|---|---|---|---|---|---|
| Morningglory | 7 | 10 | 10 | 10 | 10 | 10 | 10 | 10 | 10 | 9 | 9 |
| Nutsedge | 0 | 5 | 3 | 3 | 3 | 6 | 6 | 3 | 7 | 1 | 1 |
| Rape | 2 | 10 | 10 | 10 | 10 | 10 | 10 | 10 | 10 | 10 | 10 |
| Rice | 2 | 6 | 3 | 8 | 9 | 9 | 7 | 9 | 9 | 4 | 4 |
| Sorghum | 3 | 6 | 4 | 6 | 8 | 9 | 7 | 8 | 9 | 3 | 5 |
| Soybean | 4 | 8 | 9 | 9 | 9 | 9 | 9 | 10 | 9 | 8 | 8 |
| Sugarbeet | 2 | 10 | 9 | 10 | 10 | 10 | 10 | 10 | 10 | 10 | 10 |
| Velvetleaf | 7 | 10 | 10 | 10 | 10 | 10 | 10 | 10 | 10 | 10 | 10 |
| Wheat | 1 | 7 | 5 | 5 | 6 | 7 | 5 | 6 | 6 | 3 | 6 |
| Wild buckwheat | 6 | 10 | 10 | 10 | 10 | 10 | 10 | 10 | 10 | 10 | 10 |
| Wild oat | 1 | 5 | 4 | 6 | 6 | 8 | 4 | 7 | 5 | 2 | 8 |
| Preemergence | | | | | | | | | | | |
| Barley | 0 | 1 | 0 | 1 | 2 | 2 | 2 | 2 | 2 | 0 | 0 |
| Barnyardgrass | 0 | 3 | 0 | 6 | 7 | 8 | 6 | 8 | 8 | 0 | 3 |
| Bedstraw | 0 | 6 | 0 | 10 | 10 | 10 | 9 | 10 | 9 | 2 | 0 |
| Blackgrass | 0 | 4 | 0 | 4 | 1 | 5 | 1 | 5 | 3 | 0 | 0 |
| Cheatgrass | — | — | — | — | — | — | — | 3 | 2 | 2 | 0 |
| Chickweed | — | 10 | 9 | 8 | 8 | 10 | 4 | 10 | 6 | 2 | 0 |
| Cocklebur | 0 | 9 | 0 | 6 | 8 | 10 | 8 | 7 | 9 | 3 | 5 |
| Corn | 0 | 3 | 0 | 2 | 3 | 3 | 1 | 3 | 3 | 1 | 0 |
| Cotton | 0 | 2 | 0 | 0 | 10 | 9 | 2 | 7 | 6 | 0 | 0 |
| Crabgrass | 0 | 5 | 0 | 9 | 9 | 10 | 8 | 9 | 9 | 2 | 2 |
| Downy brome | 0 | 3 | 0 | 3 | 3 | 8 | 3 | — | — | — | — |
| Giant foxtail | 0 | 5 | 0 | 7 | 8 | 8 | 5 | 6 | 9 | 0 | 3 |
| Morningglory | 0 | 10 | 7 | 10 | 9 | 10 | 9 | 10 | 10 | 4 | 5 |
| Nutsedge | — | 0 | — | — | 7 | 3 | 4 | 3 | 8 | 3 | 3 |
| Rape | 0 | 10 | 2 | 9 | 10 | 10 | 7 | 9 | 10 | 3 | 3 |
| Rice | 0 | 0 | 0 | 2 | 3 | 5 | 2 | 3 | 5 | 0 | 0 |
| Sorghum | 0 | 2 | 0 | 2 | 5 | 4 | 2 | 3 | 5 | 0 | 0 |
| Soybean | 0 | 6 | 0 | 0 | 8 | 6 | 4 | 5 | 10 | 0 | 0 |
| Sugarbeet | 0 | 9 | 8 | 10 | 10 | 10 | 10 | 10 | 10 | 8 | 8 |
| Velvetleaf | 0 | 10 | 3 | 9 | 10 | 10 | 10 | 10 | 10 | 10 | 8 |
| Wheat | 0 | 5 | 0 | 3 | 3 | 5 | 2 | 4 | 5 | 0 | 0 |
| Wild buckwheat | 0 | 0 | 0 | 9 | 10 | 10 | 5 | 10 | 9 | 3 | 3 |
| Wild oat | 0 | 7 | 0 | 5 | 6 | 7 | 3 | 6 | 6 | 2 | 0 |

TEST B

Seeds of barnyardgrass (*Echinochloa crus-galli*), cocklebur (*Xanthium pensylvanicum*), crabgrass (*Digitaria* spp.), downy brome (*Bromus rectorum*), giant foxtail (*Setaria faberii*), morningglory (*Ipomoea* spp.), sorghum (*Sorghum bicolor*), velvetleaf (*Abutlion theophrasti*), and wild oat (*Avena fatua*) were planted into a sandy loam soil and treated preemergence, or with a soil drench (PDRN), with test chemicals dissolved in a non-phytotoxic solvent. At the same time, these crop and weed species were also treated postemergence, or sprayed to runoff (STRO), with test chemicals. Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table B, are based on a 0 to 10 scale where 0 is no effect and 10 is complete control. A dash (-) response means no test results.

TABLE B

| | COMPOUND | | | | | | | | | COMPOUND | | | | | | | |
|---|---|---|---|---|---|---|---|---|---|---|---|---|---|---|---|---|---|
| Rate 2000 g/ha | 1 | 2 | 3 | 4 | 5 | 6 | 7 | 8 | Rate 1000 g/ha | 1 | 2 | 3 | 4 | 5 | 6 | 7 | 8 |
| Preemergence | | | | | | | | | Postemergence | | | | | | | | |
| Barnyardgrass | 8 | 9 | 0 | 9 | 0 | 4 | 0 | 9 | Barnyardgrass | 8 | 5 | 4 | 10 | 3 | 2 | 3 | 9 |
| Cocklebur | 5 | 4 | 3 | 10 | 0 | 0 | 0 | 10 | Cocklebur | 7 | 7 | 2 | 10 | 4 | 4 | 1 | 10 |
| Crabgrass | 8 | 9 | 7 | 10 | 1 | 0 | 0 | 9 | Crabgrass | 8 | 6 | 4 | 10 | 3 | 2 | 2 | 10 |
| Downy brome | 2 | 0 | 0 | 10 | 0 | 0 | 0 | 0 | Downy brome | 3 | 2 | 1 | 6 | 1 | 0 | 0 | 4 |
| Giant foxtail | 9 | 9 | 4 | 10 | 3 | 0 | 0 | 9 | Giant foxtail | 9 | 7 | 3 | 10 | 4 | 3 | 3 | 10 |
| Morningglory | 3 | 4 | 2 | 10 | 0 | 0 | 0 | 10 | Morningglory | 8 | 9 | 9 | 10 | 8 | 9 | 8 | 10 |
| Sorghum | 4 | 8 | 0 | 10 | 0 | 0 | 0 | 8 | Sorghum | 3 | 4 | 3 | 9 | 2 | 3 | 3 | 6 |
| Velvetleaf | 10 | 10 | 7 | 10 | 0 | 0 | 0 | 10 | Velvetleaf | 10 | 10 | 10 | 10 | 10 | 10 | 10 | 10 |
| Wild oats | 0 | 0 | 0 | 10 | 0 | 0 | 0 | 7 | Wild oats | 2 | 3 | 1 | 9 | 3 | 2 | 2 | 7 |

TEST C

The compounds evaluated in this test were formulated in a non-phytoxic solvent and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 era for the flood test and was maintained at this level for the duration of the test. Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus rectorum*), giant foxtail (*Setaria faberii*), johnsongrass (*Sorghum halpense*), morningglory (*Ipomoea hederacea*), pigweed (*Amaranthus retroflexus*), rape (*Brassica napus*), ryegrass (*Lollum multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted One day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and Late watergrass (*Echinocloa oryzicola*) grown to the 1 and 2 leaf stage for testing. All plant species were grown using normal greenhouse practices. Visual evaluations of injury expressed on treated plants, when compared to untreated controls, were recorded approximately fourteen to twenty one days after application of the test compound. Plant response ratings, summarized in Table C, were recorded on a 0 to 100 scale where 0 is no effect and 100 is complete control. A dash (-) response means no test result.

TABLE C

| Rate 125 g/ha | Compound 9 | Rate 125 g/ha | Compound 9 |
|---|---|---|---|
| Postemergence | | Preemergence | |
| Barley | 30 | Barley | 50 |
| Barnyardgrass | 95 | Barnyardgrass | 100 |
| Blackgrass | 80 | Blackgrass | 80 |
| Chickweed | 100 | Chickweed | 100 |
| Cocklebur | 100 | Cocklebur | 95 |
| Corn | 50 | Corn | 25 |
| Cotton | 100 | Cotton | 50 |
| Crabgrass | 65 | Crabgrass | 95 |
| Downy brome | 35 | Downy brome | 0 |
| Duck salad | 20 | Galium | 55 |
| Galium | 100 | Giant foxtail | 100 |
| Giant foxtail | 95 | It. Ryegrass | 85 |
| It. Ryegrass | 80 | Johnsongrass | 95 |
| Johnsongrass | 95 | Morningglory | 100 |
| Morningglory | 100 | Rape | 50 |
| Rape | 100 | Redroot pigweed | 100 |
| Redroot pigweed | 100 | Soybean | 100 |
| Rice japonica | 100 | Speedwell | 100 |
| Soybean | 100 | Sugar beet | 100 |
| Speedwell | 100 | Velvetleaf | 100 |
| Sugar beet | 100 | Wheat | 0 |
| Umbrella sedge | 90 | Wild buckwheat | 100 |
| Velvetleaf | 100 | Wild oat | 80 |
| Watergrass-2 | 100 | | |
| Wheat | 60 | | |
| Wild buckwheat | 100 | | |
| Wild oat | 40 | | |
| Barnyardgrass-2 | 100 | | |

| | Compound | | | | | | | | | |
|---|---|---|---|---|---|---|---|---|---|---|
| Rate 62 g/ha | 4 | 8 | 9 | 10 | 11 | 12 | 13 | 14 | 15 | 16 |
| Postemergence | | | | | | | | | | |
| Barley | 35 | 30 | 30 | 40 | 65 | 35 | 60 | 50 | 20 | 30 |
| Barnyardgrass | 40 | 40 | 90 | 90 | 95 | 95 | 95 | 95 | 10 | 80 |
| Blackgrass | 50 | 40 | 70 | 45 | 80 | 50 | 95 | 75 | 40 | 20 |
| Chickweed | 95 | 95 | 100 | 100 | 100 | 90 | 100 | 85 | 75 | 25 |
| Cocklebur | 100 | 100 | 100 | 100 | 100 | 100 | 100 | 100 | 100 | 100 |
| Corn | 25 | 30 | 45 | 35 | 60 | 25 | 55 | 50 | 20 | 30 |
| Cotton | 100 | 100 | 100 | 100 | 100 | 100 | 100 | 100 | 100 | 100 |
| Crabgrass | 40 | 20 | 55 | 65 | 80 | 45 | 90 | 85 | 25 | 20 |
| Downy brome | 50 | 40 | 35 | 35 | 35 | 25 | 50 | 35 | 20 | 0 |
| Duck salad | 0 | 0 | 20 | 90 | 30 | 50 | 25 | — | 40 | 0 |
| Galium | 100 | 100 | 100 | 95 | 100 | 90 | 100 | 90 | 90 | 35 |
| Giant foxtail | 70 | 50 | 85 | 80 | 95 | 90 | 95 | 95 | 35 | 60 |
| It. ryegrass | 50 | 30 | 60 | 70 | 95 | 60 | 95 | 75 | 25 | 0 |
| Johnsongrass | 90 | 50 | 90 | 90 | 95 | 90 | 95 | 90 | 45 | 80 |
| Morningglory | 100 | 100 | 100 | 100 | 100 | 100 | 100 | 100 | 95 | 100 |
| Rape | 100 | 100 | 100 | 100 | 100 | 100 | 100 | 100 | 100 | 100 |
| Redroot pigweed | 100 | 95 | 100 | 100 | 100 | 100 | 100 | 100 | 100 | 100 |
| Rice japonica | 95 | 10 | 100 | 90 | 95 | 75 | 65 | — | 40 | 10 |

TABLE C-continued

| | | | | | | | | | | |
|---|---|---|---|---|---|---|---|---|---|---|
| Soybean | 90 | 95 | 95 | 75 | 100 | 85 | 100 | 90 | 100 | 70 |
| Speedwell | 100 | 100 | 100 | — | 100 | 100 | 100 | 100 | — | 95 |
| Sugar beet | 100 | 100 | 100 | 100 | 100 | 100 | 100 | 100 | 100 | 100 |
| Umbrella sedge | 0 | 0 | 90 | 100 | 85 | 100 | 80 | — | 65 | 0 |
| Velvetleaf | 100 | 100 | 100 | 100 | 100 | 100 | 100 | 100 | 100 | 100 |
| Watergrass-2 | 70 | 10 | 100 | 95 | 100 | 90 | 95 | — | 50 | 10 |
| Wheat | 35 | 30 | — | 35 | 75 | 40 | 75 | 35 | 40 | 20 |
| Wild buckwheat | 100 | 95 | 100 | 100 | 100 | 100 | 100 | 100 | 100 | — |
| Wild oat | 50 | 40 | 40 | 70 | 90 | 40 | 90 | 75 | 25 | 25 |
| Barnyardgrass-2 | 10 | 0 | 100 | 95 | 100 | 85 | 75 | — | 75 | 10 |
| Preemergence | | | | | | | | | | |
| Barley | 0 | 0 | 30 | 30 | 75 | 35 | 60 | 80 | 0 | 0 |
| Barnyardgrass | 60 | 10 | 100 | 95 | 100 | 85 | 100 | 95 | 20 | 0 |
| Blackgrass | 30 | 0 | 55 | 50 | 90 | 85 | 90 | 85 | 20 | 0 |
| Chickweed | 100 | 100 | 90 | 65 | 100 | 60 | 100 | 30 | 10 | 0 |
| Cocklebur | 50 | 0 | 85 | 40 | 85 | 80 | 65 | 85 | 10 | 15 |
| Corn | 20 | 10 | 25 | 35 | 60 | 25 | 40 | 30 | 0 | 0 |
| Cotton | 75 | 10 | — | 60 | 100 | 35 | 90 | 90 | 0 | 10 |
| Crabgrass | 55 | 40 | 90 | 90 | 100 | 100 | 100 | 95 | 20 | 0 |
| Downy brome | 0 | 0 | 0 | 10 | 35 | 10 | 40 | 30 | 10 | 20 |
| Galium | 100 | 35 | 40 | 30 | 100 | 35 | 100 | 70 | 60 | 20 |
| Giant foxtail | 80 | 0 | 100 | 95 | 100 | 80 | 100 | 95 | 10 | 20 |
| It. ryegrass | 55 | 0 | 10 | 70 | 95 | 10 | 95 | 90 | 10 | 20 |
| Johnsongrass | 40 | 0 | 85 | 90 | 90 | 90 | 95 | 95 | 35 | 10 |
| Morningglory | 100 | 90 | 50 | 100 | 100 | 70 | 100 | 95 | 50 | 0 |
| Rape | 100 | 30 | 20 | 90 | 100 | 20 | 100 | 100 | 20 | 10 |
| Redroot pigweed | 100 | 85 | 100 | 100 | 100 | 100 | 100 | 100 | 100 | 60 |
| Soybean | 0 | 40 | 100 | 40 | 100 | 15 | 60 | 85 | 10 | 15 |
| Speedwell | 100 | 100 | 100 | 100 | 100 | 100 | 100 | 100 | 100 | 50 |
| Sugar beet | 95 | 100 | 100 | 100 | 100 | 100 | 100 | 100 | 50 | 0 |
| Velvetleaf | 100 | 40 | 100 | 100 | 100 | 100 | 100 | 100 | 30 | 0 |
| Wheat | 0 | 0 | 0 | 30 | 45 | 20 | 50 | 55 | 10 | 0 |
| Wild buckwheat | 90 | 90 | 100 | 100 | 100 | 100 | 100 | 100 | 95 | 0 |
| Wild oat | 55 | 0 | 60 | 60 | 90 | 40 | 90 | 80 | 10 | 0 |

| | Compound | | | | | | | | | |
|---|---|---|---|---|---|---|---|---|---|---|
| Rate 31 g/ha | 4 | 8 | 9 | 10 | 11 | 12 | 13 | 14 | 15 | 16 |
| Postemergence | | | | | | | | | | |
| Barley | 35 | 30 | 30 | 40 | 50 | 30 | 50 | 40 | 20 | 20 |
| Barnyardgrass | 35 | 30 | 40 | 90 | 85 | 85 | 95 | 95 | 10 | 80 |
| Blackgrass | 40 | 30 | 35 | 40 | 80 | 35 | 80 | 65 | 35 | 20 |
| Chickweed | 80 | 80 | 100 | 100 | 100 | 70 | 100 | 70 | 60 | 25 |
| Cocklebur | 95 | 100 | 100 | 100 | 100 | 100 | 100 | 100 | 100 | 80 |
| Corn | 25 | 25 | 30 | 30 | 35 | 20 | 35 | 35 | 15 | 25 |
| Cotton | 100 | 100 | 100 | 100 | 100 | 100 | 100 | 100 | 100 | 100 |
| Crabgrass | 30 | 20 | 55 | 50 | 65 | 40 | 45 | 50 | 20 | 0 |
| Downy brome | 40 | 30 | 10 | 35 | 30 | 20 | 35 | 35 | 20 | 0 |
| Duck salad | 0 | 0 | 15 | 85 | 30 | 0 | 0 | 45 | 25 | 0 |
| Galium | 100 | 100 | 100 | — | 100 | 80 | 100 | 90 | 85 | 0 |
| Giant foxtail | 50 | 45 | 85 | 70 | 80 | 40 | 90 | 90 | 25 | 40 |
| It. ryegrass | 40 | 25 | 30 | 60 | 90 | 30 | 80 | 70 | 20 | 0 |
| Johnsongrass | 90 | 40 | 45 | 80 | 95 | 50 | 90 | 90 | 30 | 70 |
| Morningglory | 100 | 100 | 100 | 100 | 100 | 100 | 100 | 100 | 90 | 85 |
| Rape | 100 | 100 | 100 | 100 | 100 | 100 | 100 | 100 | 100 | 50 |
| Redroot pigweed | 100 | — | 100 | 100 | 100 | 100 | 100 | 100 | 100 | 85 |
| Rice japonica | 85 | 10 | 90 | 70 | 70 | 45 | 40 | 65 | 35 | 10 |
| Soybean | 90 | 95 | 95 | 65 | 95 | 85 | 100 | 90 | 55 | 60 |
| Speedwell | 100 | 100 | 100 | — | 100 | 100 | — | 100 | — | 95 |
| Sugar beet | 100 | 100 | 100 | 100 | 100 | 100 | 100 | 100 | 100 | 100 |
| Umbrella sedge | 0 | 0 | 70 | 100 | 85 | 85 | 40 | 80 | 0 | 0 |
| Velvetleaf | 100 | 100 | 100 | 100 | 100 | 100 | 100 | 100 | 100 | 100 |
| Watergrass-2 | 55 | 0 | 90 | 95 | 100 | 60 | 70 | 85 | 45 | 10 |
| Wheat | 30 | 30 | 30 | 35 | 50 | 35 | 60 | 35 | 35 | 20 |
| Wild buckwheat | 100 | 95 | 100 | 100 | 100 | 100 | 100 | 100 | 100 | 100 |
| Wild oat | 35 | 30 | 30 | 65 | 90 | 30 | 80 | 70 | 20 | 10 |
| Barnyardgrass-2 | 0 | 0 | 100 | 90 | 95 | 80 | 60 | 90 | 65 | 10 |
| Preemergence | | | | | | | | | | |
| Barley | 0 | 0 | 20 | 20 | 70 | 35 | 40 | 60 | 0 | 0 |
| Barnyardgrass | 20 | 0 | 95 | 50 | 100 | 80 | 95 | 95 | 15 | 0 |
| Blackgrass | 20 | 0 | 35 | 35 | 60 | 30 | 70 | 70 | 0 | 0 |
| Chickweed | 20 | 80 | 80 | 50 | 100 | 30 | 75 | 0 | 0 | 0 |
| Cocklebur | 20 | 0 | 60 | 35 | 65 | 30 | 35 | 50 | 0 | 10 |
| Corn | 0 | 0 | 20 | 25 | 55 | 25 | 30 | 20 | — | 0 |
| Cotton | 40 | 10 | 30 | 50 | 100 | 20 | 50 | 60 | 0 | 0 |

TABLE C-continued

| | | | | | | | | | | |
|---|---|---|---|---|---|---|---|---|---|---|
| Crabgrass | 70 | 20 | 80 | 60 | 100 | 55 | 90 | 70 | 10 | 0 |
| Downy brome | 0 | 0 | 0 | 0 | 10 | 0 | 30 | 10 | 0 | 10 |
| Galium | 70 | — | 20 | 30 | 100 | 10 | 100 | 70 | 10 | 0 |
| Giant foxtail | 70 | 0 | 95 | 85 | 100 | 60 | 95 | 90 | 0 | 0 |
| It. ryegrass | 0 | 0 | 0 | 30 | 75 | — | 70 | 20 | 0 | 10 |
| Johnsongrass | 30 | 0 | 50 | 75 | 90 | 40 | 95 | 70 | 15 | 0 |
| Morningglory | 20 | 20 | 50 | 75 | 100 | 50 | 50 | 75 | 20 | 0 |
| Rape | 0 | 0 | 0 | 45 | 100 | — | 90 | 100 | 0 | 0 |
| Redroot pigweed | 100 | 50 | 100 | 100 | 100 | 100 | 100 | 100 | 90 | 30 |
| Soybean | 0 | 20 | 100 | 10 | 15 | 10 | 60 | 75 | 0 | 0 |
| Speedwell | 100 | 95 | 100 | 60 | 100 | 100 | 100 | 100 | 90 | — |
| Sugar beet | 95 | 0 | 100 | 100 | 100 | 60 | 100 | 100 | 10 | 0 |
| Velvetleaf | 100 | 0 | 100 | 100 | 100 | 100 | 100 | 100 | 20 | 0 |
| Wheat | 0 | 0 | 0 | 20 | 25 | 10 | 30 | 10 | 0 | 0 |
| Wild buckwheat | 55 | 90 | 100 | 100 | 100 | 90 | 100 | 100 | 30 | 0 |
| Wild oat | 25 | 0 | 30 | 30 | 85 | 40 | 50 | 65 | 0 | 0 |

| | Compound | | | | | | | | | |
|---|---|---|---|---|---|---|---|---|---|---|
| Rate 16 g/ha | 4 | 8 | 9 | 10 | 11 | 12 | 13 | 14 | 15 | 16 |
| Postemergence | | | | | | | | | | |
| Barley | 30 | 25 | 30 | 35 | 35 | 25 | 40 | 30 | — | 10 |
| Barnyardgrass | 30 | 25 | 30 | 30 | 85 | 35 | 70 | 70 | 10 | 65 |
| Blackgrass | 40 | — | 30 | 40 | 55 | 35 | 75 | 60 | 30 | 20 |
| Chickweed | 70 | 70 | 80 | 90 | 95 | 65 | 90 | 70 | 55 | 25 |
| Cocklebur | 90 | 95 | 100 | 85 | 100 | 95 | 100 | 100 | 95 | — |
| Corn | 20 | 20 | 20 | 25 | 25 | 15 | 20 | 20 | 10 | 25 |
| Cotton | 100 | 100 | 100 | 100 | 100 | 100 | 100 | 100 | 100 | 100 |
| Crabgrass | 25 | 15 | 30 | 30 | 45 | 25 | 35 | 45 | 20 | 0 |
| Downy brome | 30 | 25 | 10 | 30 | 25 | 10 | 30 | 25 | 15 | 0 |
| Duck salad | 0 | 0 | 10 | 50 | 0 | 0 | 0 | 35 | 0 | 0 |
| Galium | 90 | 95 | 100 | 90 | 85 | 80 | 85 | 90 | 65 | 0 |
| Giant foxtail | 45 | 35 | 60 | 55 | 80 | 20 | 80 | 55 | 25 | 40 |
| It. ryegrass | 25 | 20 | 20 | 30 | 35 | 20 | 40 | 35 | 20 | 0 |
| Johnsongrass | 85 | 30 | 40 | 65 | 70 | 35 | 60 | 50 | 25 | 70 |
| Morningglory | 100 | 100 | 100 | 100 | 100 | 100 | 100 | 100 | — | 85 |
| Rape | 100 | 100 | 100 | — | 100 | 100 | 100 | 100 | 90 | 40 |
| Redroot pigweed | 100 | 90 | 100 | 100 | 100 | 100 | 100 | 100 | 100 | 80 |
| Rice japonica | 55 | 0 | 50 | 25 | 30 | 30 | 35 | 60 | 20 | 10 |
| Soybean | 85 | 95 | 85 | 65 | 85 | 75 | 85 | 80 | 55 | 45 |
| Speedwell | 100 | 90 | 100 | — | — | 100 | — | 100 | 70 | 90 |
| Sugar beet | 100 | 100 | 100 | 100 | 100 | 100 | 100 | 100 | 100 | 65 |
| Umbrella sedge | 0 | 0 | 10 | 90 | 35 | 20 | 0 | 50 | 0 | 0 |
| Velvetleaf | 100 | 100 | 100 | 100 | 100 | 100 | 100 | 100 | 100 | 100 |
| Watergrass-2 | 0 | 0 | 55 | 35 | 70 | 30 | 70 | 35 | 25 | 0 |
| Wheat | 25 | 25 | 20 | 25 | 40 | 35 | 40 | 30 | 35 | 10 |
| Wild buckwheat | 90 | 80 | 100 | 100 | 100 | 100 | 100 | 100 | 100 | 85 |
| Wild oat | 30 | 30 | 20 | 40 | 55 | 30 | 45 | 40 | 20 | 10 |
| Barnyardgrass-2 | 0 | 0 | 95 | 40 | 65 | 20 | 25 | 60 | 50 | 0 |
| Preemergence | | | | | | | | | | |
| Barley | 0 | 0 | 0 | 0 | 40 | 20 | 30 | 30 | 0 | 0 |
| Barnyardgrass | 20 | 0 | 85 | 30 | 65 | 35 | 90 | 50 | 10 | 0 |
| Blackgrass | 20 | 0 | 10 | 25 | 40 | 10 | 50 | 50 | 0 | 0 |
| Chickweed | 20 | 10 | 70 | 35 | 70 | 0 | — | 0 | — | 0 |
| Cocklebur | 0 | 0 | 35 | 10 | 60 | 20 | 20 | 35 | 0 | 0 |
| Corn | 0 | 0 | 10 | 0 | 25 | 10 | 20 | 0 | 0 | 0 |
| Cotton | — | 0 | 25 | 20 | 60 | 15 | 45 | 10 | 0 | 0 |
| Crabgrass | 20 | 10 | 30 | 30 | 75 | 35 | 70 | 70 | 10 | 0 |
| Downy brome | 0 | 0 | 0 | 0 | 0 | 0 | 20 | 0 | 0 | 0 |
| Galium | 0 | 0 | 0 | 10 | 30 | 0 | 100 | 30 | 0 | 0 |
| Giant foxtail | 50 | 0 | 90 | 65 | 50 | 50 | 90 | 35 | 0 | 0 |
| It. ryegrass | 0 | 0 | 0 | 10 | 20 | 0 | 50 | 10 | 0 | 0 |
| Johnsongrass | 10 | 0 | 20 | 20 | 65 | 20 | 55 | 35 | 0 | 0 |
| Morningglory | 0 | 10 | 20 | 30 | 100 | 40 | 50 | 30 | 10 | 0 |
| Rape | 0 | 0 | 0 | 10 | 20 | 10 | 85 | 85 | 0 | 0 |
| Redroot pigweed | 100 | 30 | 100 | 100 | 100 | 90 | 100 | 100 | — | 30 |
| Soybean | 0 | — | 35 | 0 | 10 | 0 | 35 | 0 | 0 | 0 |
| Speedwell | 100 | 0 | 100 | 40 | 100 | 100 | 100 | 100 | 50 | 0 |
| Sugar beet | 35 | 0 | 100 | 60 | 75 | 0 | 100 | 100 | 0 | 0 |
| Velvetleaf | 70 | 0 | 55 | 100 | 100 | 100 | 100 | 100 | 0 | 0 |
| Wheat | 0 | 0 | 0 | 0 | 20 | 0 | 20 | 10 | 0 | 0 |
| Wild buckwheat | 0 | 0 | 50 | 100 | 100 | 90 | 100 | 100 | — | 0 |
| Wild oat | 0 | 0 | 10 | 20 | 60 | 35 | 30 | 30 | 0 | 0 |

TABLE C-continued

| Rate 8 g/ha | Compound | | | | | | | | |
|---|---|---|---|---|---|---|---|---|---|
| | 4 | 8 | 10 | 11 | 12 | 13 | 14 | 15 | 16 |
| Postemergence | | | | | | | | | |
| Barley | 25 | 20 | 35 | 25 | 25 | 35 | 25 | 20 | 0 |
| Barnyardgrass | 30 | 20 | 15 | 40 | 35 | 40 | 50 | 10 | 50 |
| Blackgrass | 35 | 25 | 35 | 40 | 35 | 70 | 35 | 25 | 20 |
| Chickweed | 40 | 60 | 80 | 90 | 55 | 85 | 45 | 50 | 25 |
| Cocklebur | 90 | 90 | 85 | 90 | 90 | 95 | 90 | 90 | 65 |
| Corn | 15 | 15 | 25 | 25 | 15 | 20 | 15 | 10 | 10 |
| Cotton | 100 | 100 | 100 | 100 | 100 | 100 | 100 | 100 | 100 |
| Crabgrass | 20 | 10 | 20 | 10 | 25 | 30 | 30 | 15 | 0 |
| Downy brome | 30 | 20 | 25 | 25 | 10 | 30 | 20 | 10 | 0 |
| Duck salad | 0 | 0 | 40 | 0 | 0 | 0 | 0 | 0 | 0 |
| Galium | 60 | 60 | 75 | 75 | 75 | 70 | 35 | 55 | 0 |
| Giant foxtail | 30 | 35 | 20 | 35 | 20 | 35 | 40 | 25 | 20 |
| It. ryegrass | 20 | 20 | 0 | 30 | 20 | 20 | 20 | 20 | 0 |
| Johnsongrass | 40 | 25 | 65 | 45 | 30 | 25 | 25 | 20 | 60 |
| Morningglory | 95 | 100 | 80 | 100 | 90 | 95 | 95 | 90 | 75 |
| Rape | 95 | 100 | 100 | 100 | 100 | 100 | 100 | 90 | 20 |
| Redroot pigweed | 95 | 90 | 100 | 100 | 100 | 100 | 90 | 100 | 80 |
| Rice japonica | 40 | 0 | 15 | 20 | 20 | 30 | 30 | 0 | 0 |
| Soybean | 50 | 90 | 65 | 80 | 50 | 85 | 80 | 55 | 35 |
| Speedwell | 100 | 90 | — | — | 100 | 70 | — | 50 | 80 |
| Sugar beet | 100 | 100 | 100 | 100 | 100 | 100 | 90 | 100 | 50 |
| Umbrella sedge | 0 | 0 | 80 | 20 | 20 | 0 | 40 | 0 | 0 |
| Velvetleaf | 100 | 100 | 100 | 100 | 100 | 100 | 100 | 100 | 100 |
| Watergrass-2 | 0 | 0 | 30 | 25 | 25 | 45 | 25 | 10 | 0 |
| Wheat | 20 | 20 | 25 | 25 | 30 | 40 | 20 | 20 | 0 |
| Wild buckwheat | 75 | 80 | 100 | 100 | 100 | 100 | 100 | 100 | 80 |
| Wild oat | 30 | 20 | 25 | 45 | 30 | 40 | 30 | 20 | 10 |
| Barnyardgrass-2 | 0 | 0 | 25 | 25 | 0 | 20 | 30 | 0 | 0 |
| Preemergence | | | | | | | | | |
| Barley | 0 | 0 | 0 | 20 | 20 | 0 | 0 | 0 | 0 |
| Barnyardgrass | 10 | 0 | 0 | 35 | 10 | 40 | 30 | 10 | 0 |
| Blackgrass | 0 | 0 | 25 | 20 | 10 | 10 | 0 | 0 | 0 |
| Chickweed | 20 | 0 | 20 | — | 0 | 30 | 0 | 0 | 0 |
| Cocklebur | 0 | 0 | 0 | 25 | 0 | 0 | 15 | 0 | 0 |
| Corn | 0 | 0 | 0 | 25 | 10 | 10 | 0 | 0 | 0 |
| Cotton | — | 0 | 10 | 30 | 10 | 30 | 0 | 0 | 0 |
| Crabgrass | 0 | 0 | 10 | 25 | 10 | 40 | 45 | 0 | 0 |
| Downy brome | 0 | 0 | 0 | 0 | 0 | 0 | 0 | 0 | 0 |
| Galium | 0 | 0 | 10 | 0 | 0 | 0 | 0 | 0 | 0 |
| Giant foxtail | 0 | 0 | 30 | 50 | 50 | 40 | 20 | 0 | 0 |
| It. ryegrass | 0 | 0 | 0 | 0 | 0 | 10 | 0 | 0 | 0 |
| Johnsongrass | 0 | 0 | 0 | 30 | 10 | 20 | 25 | 0 | 0 |
| Morningglory | 0 | 10 | 10 | 60 | 30 | 20 | 20 | 10 | 0 |
| Rape | 0 | 0 | 0 | 0 | 0 | 10 | 20 | 0 | 0 |
| Redroot pigweed | 30 | 20 | 80 | 100 | 70 | 100 | 90 | 65 | 0 |
| Soybean | 0 | 10 | 0 | 10 | 0 | 10 | 0 | 0 | 0 |
| Speedwell | 100 | — | — | 100 | 95 | 100 | 100 | — | 0 |
| Sugar beet | 35 | 0 | 30 | 55 | 0 | 20 | 0 | 0 | 0 |
| Velvetleaf | 45 | 0 | 20 | 100 | 30 | 100 | 100 | 0 | 0 |
| Wheat | 0 | 0 | 0 | 0 | 0 | 0 | 0 | 0 | 0 |
| Wild buckwheat | 0 | 0 | 100 | 95 | 35 | 90 | 100 | 0 | 0 |
| Wild oat | 0 | 0 | 10 | 10 | 35 | 20 | 20 | 0 | 0 |

| Rate 4 g/ha | Compound | | Rate 4 g/ha | Compound | |
|---|---|---|---|---|---|
| | 13 | 14 | | 13 | 14 |
| Postemergence | | | Preemergence | | |
| Barley | 35 | 20 | Barley | 0 | 0 |
| Barnyardgrass | 30 | 15 | Barnyardgrass | 30 | 20 |
| Blackgrass | 60 | 20 | Blackgrass | — | 0 |
| Chickweed | 85 | 35 | Chickweed | — | 0 |
| Cocklebur | 90 | 90 | Cocklebur | 0 | 0 |
| Corn | 20 | 10 | Corn | 10 | 0 |
| Cotton | 100 | 100 | Cotton | 10 | 0 |
| Crabgrass | 20 | 20 | Crabgrass | 0 | 20 |
| Downy brome | 20 | 10 | Downy brome | 0 | 0 |
| Duck salad | — | 0 | Galium | 9 | 0 |
| Galium | 50 | 30 | Giant foxtail | 35 | 0 |
| Giant foxtail | 25 | 35 | It. ryegrass | 10 | 0 |
| It. ryegrass | 20 | 10 | Johnsongrass | 10 | 0 |

TABLE C-continued

| | | | | | |
|---|---|---|---|---|---|
| Johnsongrass | 25 | 20 | Morningglory | 10 | 0 |
| Morningglory | 90 | 90 | Rape | 0 | 0 |
| Rape | 100 | 95 | Redroot pigweed | 95 | 30 |
| Redroot pigweed | 100 | 90 | Soybean | 0 | 0 |
| Rice japonica | — | 0 | Speedwell | 100 | 95 |
| Soybean | 55 | 75 | Sugar beet | 20 | 0 |
| Speedwell | 60 | — | Velvetleaf | 40 | 0 |
| sugar beet | 90 | 65 | Wheat | 0 | 0 |
| Umbrella sedge | — | 25 | Wild buckwheat | 40 | 30 |
| Velvetleaf | 100 | 100 | Wild oat | 0 | 20 |
| Watergrass-2 | — | 0 | | | |
| Wheat | 40 | 15 | | | |
| Wild buckwheat | 95 | 100 | | | |
| Wild oat | 40 | 20 | | | |
| Barnyardgrass-2 | — | 10 | | | |

TEST D

Seeds of barnyardgrass (*Echinochloa crus-galli*), bindweed (*Convolvulus althaeoides*), black nightshade (*Solanum ptycanthum dunal*), cassia (*Cassia obtusifolia* ), cocklebur (*Xanthium pensylvanicum*), common ragweed (*Ambrosia artemisiifolia*), tom (*Zea mays*), cotton (*Gossypium hirsutam*), crabgrass (Digitaria spp.), fall panicum (*Panicum dichotomiflorum*), giant foxtail (*Setaria faberii*), green foxtail (*Setaria viridis*), jimsonweed (*Datura stramonium*), johnson grass (*Sorghum halepense*), morningglory (Ipomoea spp.), pigweed (*Amaranthus retroflexus*), prickly sida (*Sida spinosa*), shattercane (*Sorghum vulgare*), signalgrass (*Brachiaria platyphylla*), smartweed (*Polygonum pensylvanicum*), soybean (*Glycine max*), sunflower (*Helianthus annuus*), velvetleaf (*Abutilon theophrasti*), wild proso (*Pancium miliaceum*), wooly cupgrass (*Eriochloa villosa*), yellow foxtail (*Setaria lutescens*), and purple nutsedge (*Cyperus rotundus*) tubers were planted into a matapeake sandy loam soil. These crops and weeds were grown in the greenhouse until the plants ranged in height from two to eighteen em (one to four leaf stage), then treated postemergence with the test chemicals dissolved in a nonphytotoxic solvent. Pots receiving these postemergence treatments were placed in the greenhouse and maintained according to routine greenhouse procedures. Treated plants and untreated controls were maintained in the greenhouse approximately 14–21 days after application of the test compound. Visual evaluations of plant injury responses were then recorded. Plant response ratings, summarized in Table D, are reported on a 0 to 100 scale where 0 is no effect and 100 is complete control.

TABLE D

| Rate 140 g/ha Preemergence | Compound 9 | Rate 70 g/ha Postemergence | Compound 9 |
|---|---|---|---|
| Barnyardgrass | 95 | Barnyardgrass | 45 |
| Bindweed | 100 | Bindweed | 100 |
| Blk nightshade | 100 | Blk nightshade | 70 |
| Cassia | 20 | Cassia | 100 |
| Cocklebur | 55 | Cocklebur | 90 |
| Corn | 65 | Corn | 35 |
| Cotton | 20 | Cotton | 100 |
| Crabgrass | 100 | Crabgrass | 25 |
| Fall panicum | 95 | Fall panicum | 35 |
| Giant foxtail | 100 | Giant foxtail | 40 |
| Green foxtail | 100 | Green foxtail | 40 |
| Jimsonweed | 100 | Jimsonweed | 100 |
| Johnson grass | 90 | Johnson grass | 40 |
| Morningglory | 85 | Morningglory | 100 |
| Nutsedge | 40 | Nutsedge | 20 |

TABLE D-continued

| | | | |
|---|---|---|---|
| Pigweed | 100 | Pigweed | 100 |
| Prickly sida | 100 | Prickly sida | 95 |
| Ragweed | 90 | Ragweed | 75 |
| Shattercane | 45 | Shattercane | 45 |
| Signalgrass | 100 | Signalgrass | 55 |
| Smartweed | 100 | Smartweed | 75 |
| Soybean | 20 | Soybean | 90 |
| Sunflower | 65 | Sunflower | 100 |
| Velvetleaf | 100 | Velvetleaf | 100 |
| Wild proso | 100 | Wild proso | 40 |
| Yellow foxtail | 100 | Wooly cup grass | 35 |
| | | Yellow foxtail | 45 |

| Rate 70 g/ha | Compound | Rate 35 g/ha | Compound | | |
|---|---|---|---|---|---|
| Preemergence | 9 | Postemergence | 4 | 8 | 9 |
| Barnyardgrass | 75 | Barnyardgrass | 0 | 10 | 35 |
| Bindweed | 100 | Bindweed | 100 | 100 | 60 |
| Blk nightshade | 100 | Blk nightshade | 100 | 85 | 35 |
| Cassia | 0 | Cassia | 100 | 100 | 65 |
| Cocklebur | 45 | Cocklebur | 100 | 100 | 65 |
| Corn | 20 | Corn | 25 | 35 | 30 |
| Cotton | 0 | Cotton | 100 | 100 | 100 |
| Crabgrass | 85 | Crabgrass | 0 | 10 | 25 |
| Fall panicum | 95 | Fall panicum | 0 | 0 | 30 |
| Giant foxtail | 100 | Giant foxtail | 0 | 15 | 30 |
| Green foxtail | 100 | Green foxtail | 0 | 15 | 30 |
| Jimsonweed | 65 | Jimsonweed | 100 | 100 | 75 |
| Johnson grass | 60 | Johnson grass | 0 | 15 | 35 |
| Morningglory | 20 | Morningglory | 100 | 100 | 65 |
| Nutsedge | 20 | Nutsedge | 0 | 0 | 15 |
| Pigweed | 100 | Pigweed | 100 | 85 | 90 |
| Prickly sida | 100 | Prickly sida | 65 | 75 | 35 |
| Ragweed | 55 | Ragweed | 100 | 90 | 20 |
| Shattercane | 25 | Shattercane | 15 | 10 | 30 |
| Signalgrass | 85 | Signalgrass | 0 | 0 | 35 |
| Smartweed | 100 | Smartweed | 100 | 100 | 25 |
| Soybean | 0 | Soybean | 80 | 80 | 50 |
| Sunflower | 30 | Sunflower | 70 | 100 | 60 |
| Velvetleaf | 100 | Velvetleaf | 100 | 100 | 75 |
| Wild proso | 85 | Wild proso | 15 | 0 | 35 |
| Yellow foxtail | 95 | Wooly cup grass | 15 | 0 | 30 |
| | | Yellow foxtail | 0 | 15 | 30 |

| Rate 35 g/ha | Compound | Rate 17 g/ha | Compound | | |
|---|---|---|---|---|---|
| Preemergence | 9 | Postemergence | 4 | 8 | 9 |
| Barnyardgrass | 55 | Barnyardgrass | 0 | 5 | 35 |
| Bindweed | 20 | Bindweed | 85 | 100 | 40 |
| Blk nightshade | 100 | Blk nightshade | 95 | 75 | 30 |
| Cassia | 0 | Cassia | 80 | 75 | 55 |
| Cocklebur | 30 | Cocklebur | 85 | 100 | 60 |
| Corn | 0 | Corn | 20 | 30 | 25 |
| Cotton | 0 | Cotton | 100 | 100 | 100 |
| Crabgrass | 55 | crabgrass | 0 | 5 | 15 |

TABLE D-continued

| | | | | |
|---|---|---|---|---|
| Fall panicum | 95 | Fall panicum | 0 | 0 | 25 |
| Giant foxtail | 50 | Giant foxtail | 0 | 15 | 25 |
| Green foxtail | 50 | Green foxtail | 0 | 15 | 25 |
| Jimsonweed | 10 | Jimsonweed | 100 | 95 | 70 |
| Johnson grass | 15 | Johnson grass | 0 | 10 | 30 |
| Morningglory | 0 | Morningglory | 100 | 100 | 40 |
| Nutsedge | 0 | Nutsedge | 0 | 0 | 15 |
| Pigweed | 100 | Pigweed | 90 | 75 | 90 |
| Prickly sida | 100 | Prickly sida | 55 | 65 | 25 |
| Ragweed | 45 | Ragweed | 100 | 75 | 15 |
| Shattercane | 15 | Shattercane | 10 | 5 | 25 |
| Signalgrass | 0 | Signalgrass | 0 | 0 | 30 |
| Smartweed | 100 | Smartweed | 100 | 90 | 25 |
| Soybean | 0 | Soybean | 70 | 75 | 35 |
| Sunflower | 0 | Sunflower | 65 | 85 | 55 |
| Velvetleaf | 65 | Velvetleaf | 100 | 100 | 55 |
| Wild proso | 25 | Wild proso | 10 | 0 | 30 |
| Yellow foxtail | 40 | Wooly cup grass | 10 | 0 | 25 |
| | | Yellow foxtail | 0 | 10 | 25 |

| Rate 17 g/ha | Compound | Rate 8 g/ha | Compound | | |
|---|---|---|---|---|---|
| Preemergence | 9 | Postemergence | 4 | 8 | 9 |
| Barnyardgrass | 15 | Barnyardgrass | 0 | 0 | 30 |
| Bindweed | 0 | Bindweed | 70 | 80 | 35 |
| Blk nightshade | 100 | Blk nightshade | 60 | 70 | 25 |
| Cassia | 0 | Cassia | 60 | 65 | 50 |
| Cocklebur | 15 | Cocklebur | 55 | 80 | 20 |
| Corn | 0 | Corn | 20 | 20 | 25 |
| Cotton | 0 | Cotton | 100 | 100 | 100 |
| Crabgrass | 15 | Crabgrass | 0 | 0 | 10 |
| Fall panicum | 35 | Fall panicum | 0 | 0 | 20 |
| Giant foxtail | 10 | Giant foxtail | 0 | 10 | 25 |
| Green foxtail | 10 | Green foxtail | 0 | 10 | 20 |
| Jimsonweed | 0 | Jimsonweed | 100 | 80 | 65 |
| Johnson grass | 0 | Johnson grass | 0 | 0 | 25 |
| Morningglory | 0 | Morningglory | 100 | 65 | 35 |
| Nutsedge | 0 | Nutsedge | 0 | 0 | 0 |
| Pigweed | 100 | Pigweed | 65 | 70 | 85 |
| Prickly sida | 65 | Prickly sida | 45 | 45 | 20 |
| Ragweed | 15 | Ragweed | 65 | 65 | 10 |
| Shattercane | 10 | Shattercane | 0 | 0 | 20 |
| Signalgrass | 0 | Signalgrass | 0 | 0 | 25 |
| Smartweed | 100 | Smartweed | 55 | 80 | 20 |
| Soybean | 0 | Soybean | 65 | 70 | 20 |
| Sunflower | 0 | Sunflower | 60 | 55 | 50 |
| Velvetleaf | 40 | Velvetleaf | 100 | 65 | 45 |
| Wild proso | 15 | Wild proso | 0 | 0 | 25 |
| Yellow foxtail | 10 | Wooly cup grass | 5 | 0 | 20 |
| | | Yellow foxtail | 0 | 5 | 20 |

| Rate 8 g/ha | Compound | Rate 4 g/ha | Compound | | |
|---|---|---|---|---|---|
| Preemergence | 9 | Postemergence | 4 | 8 | 9 |
| Barnyardgrass | 0 | Barnyardgrass | 0 | 0 | 15 |
| Bindweed | 0 | Bindweed | 25 | 65 | 15 |
| Blk nightshade | 100 | Blk nightshade | 40 | 60 | 20 |
| Cassia | 0 | Cassia | 20 | 35 | 10 |
| Cocklebur | 0 | Cocklebur | 45 | 65 | 15 |
| Corn | 0 | Corn | 15 | 15 | 20 |
| Cotton | 0 | Cotton | 75 | 100 | 100 |
| Crabgrass | 0 | Crabgrass | 0 | 0 | 0 |
| Fall panicum | 0 | Fall panicum | 0 | 0 | 10 |
| Giant foxtail | 0 | Giant foxtail | 0 | 0 | 10 |
| Green foxtail | 0 | Green foxtail | 0 | 0 | 10 |
| Jimsonweed | 0 | Jimsonweed | 100 | 65 | 10 |
| Johnson grass | 0 | Johnson grass | 0 | 0 | 15 |
| Morningglory | 0 | Morningglory | 95 | 60 | 10 |
| Nutsedge | 0 | Nutsedge | 0 | 0 | 0 |
| Pigweed | 90 | Pigweed | 55 | 55 | 10 |
| Prickly sida | 20 | Prickly sida | 25 | 15 | 0 |
| Ragweed | 0 | Ragweed | 35 | 40 | 0 |
| Shattercane | 0 | Shattercane | 0 | 0 | 10 |
| Signalgrass | 0 | Signalgrass | 0 | 0 | 15 |
| Smartweed | 55 | Smartweed | 0 | 60 | 15 |
| Soybean | 0 | Soybean | 40 | 60 | 15 |
| Sunflower | 0 | Sunflower | 55 | 45 | 40 |
| Velvetleaf | 15 | Velvetleaf | 55 | 45 | 15 |
| Wild proso | 0 | Wild proso | 0 | 0 | 20 |
| Yellow foxtail | 0 | Wooly cup grass | 0 | 0 | 15 |
| | | Yellow foxtail | 0 | 0 | 10 |

| Rate 2 g/ha | Compound | |
|---|---|---|
| Postemergence | 4 | 8 |
| Barnyardgrass | 0 | 0 |
| Bindweed | 0 | 45 |
| Blk nightshade | 0 | 40 |
| Cassia | 10 | 10 |
| Cocklebur | 30 | 50 |
| Corn | 10 | 10 |
| Cotton | — | 100 |
| Crabgrass | 0 | 0 |
| Fall panicum | 0 | 0 |
| Giant foxtail | 0 | 0 |
| Green foxtail | 0 | 0 |
| Jimsonweed | 100 | 55 |
| Johnson grass | 0 | 0 |
| Morningglory | 35 | 40 |
| Nutsedge | 0 | 0 |
| Pigweed | 45 | 35 |
| Prickly sida | 0 | 0 |
| Ragweed | 30 | 25 |
| Shattercane | 0 | 0 |
| Signalgrass | 0 | 0 |
| Smartweed | 0 | 35 |
| Soybean | 10 | 15 |
| Sunflower | 35 | 20 |
| Velvetleaf | 45 | 20 |
| Wild proso | 0 | 0 |
| Wooly cup grass | 0 | 0 |
| Yellow foxtail | 0 | 0 |

We claim:

1. A compound of the formula

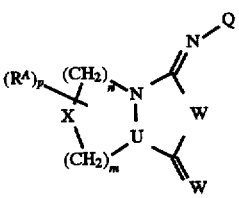

wherein:

X is selected from the group O, S, S(O), S(O)$_2$, CHOCH$_2$F, CHOCHF$_2$, CHOCF$_3$, CHOCH$_2$CF$_3$ and NR$^4$;

m and n are independently 1 or 2, where m+n=2 or 3;

p is 0 to 9;

U is N or CH;

W is independently O or S;

R$^4$ is independently selected from the group halogen, C$_1$–C$_4$ alkyl, cyano, C$_1$–C$_4$ haloalkyl, C$_3$–C$_4$ alkenyl, C$_1$–C$_3$ alkylthio, C$_1$–C$_3$ haloalkylthio, C$_2$–C$_4$ alkylcarbonyl, OR$^3$, C$_2$–C$_6$ alkyloxycarbonyl, C$_2$–C$_6$ haloalkoxycarbonyl, and C$_3$–C$_8$ alkoxycarbonylalkyl; or, two R$^4$ groups on the same carbon atom, together with this carbon, are C=O;

R$^3$ is selected from the group hydrogen, C$_1$–C$_4$ alkyl, C$_1$–C$_4$ haloalkyl, C$_2$–C$_4$ alkylcarbonyl and C$_2$–C$_4$ haloalkylcarbonyl;

R$^4$ is selected from the group hydrogen, C$_1$–C$_3$ alkyl, C$_1$–C$_3$ haloalkyl, C$_2$–C$_4$ alkylcarbonyl, C$_2$–C$_4$ haloalkoxycarbonyl and C$_2$–C$_4$ alkoxycarbonyl;

provided that when X is CHOCH$_2$F, CHOCHF$_2$, CHOCF$_3$, or CHOCH$_2$CF$_3$, m and n are 1, and U is N, then p is 1 to 5 and at least one R$^4$ is other than alkyl;

Q is selected from the group

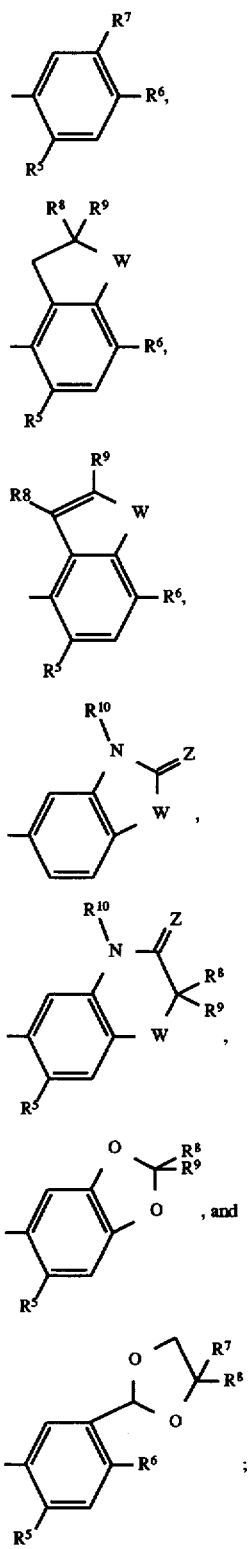

Z is O or S;
$R^5$ is hydrogen or halogen;
$R^6$ is selected from the group $C_1$–$C_2$ alkyl, $C_1$–$C_2$ haloalkyl, $OCH_3$, $SCH_3$, $OCHF_2$, halogen, CN and $NO_2$;
$R^7$ is selected from the group hydrogen, $C_1$–$C_8$ alkyl, $C_1$–$C_8$ haloalkyl, halogen, $OR^{11}$, $SR^{11}$, $S(O)_qR^{11}$, $COR^{11}$, $CO_2R^{11}$, $C(O)SR^{11}$, $C(O)NR^{12}R^{13}$, CHO and $NHSO_2NHR^{16}$;

$R^8$ is selected from the group hydrogen, $C_1$–$C_3$ alkyl, $C_1$–$C_3$ haloalkyl and halogen;

$R^9$ is selected from the group hydrogen, $C_1$–$C_3$ alkyl, $C_1$–$C_3$ haloalkyl and halogen; or, when Q is Q-2 or Q-6, $R^8$ and $R^9$ together with the carbon to which they are bonded is additionally selected from C=O;

$R^{10}$ is selected from the group $C_1$–$C_6$ alkyl, $C_1$–$C_6$ haloalkyl, $C_2$–$C_6$ alkoxyalkyl, $C_3$–$C_6$ alkenyl and $C_3$–$C_6$ alkynyl;

$R^{11}$ is selected from the group $C_1$–$C_8$ alkyl, $C_3$–$C_8$ cycloalkyl, $C_3$–$C_8$ alkenyl, $C_3$–$C_8$ alkynyl, $C_1$–$C_8$ haloalkyl, $C_2$–$C_8$ alkoxyalkyl, $C_2$–$C_8$ alkylthioalkyl, $C_2$–$C_8$ alkylsulphinylalkyl, $C_2$–$C_8$ alkylsulphonylalkyl, $C_3$–$C_8$ alkoxyalkoxyalkyl, $C_4$–$C_8$ cycloalkylalkyl, $C_2$–$C_4$ carboxyalkyl, $C_3$–$C_8$ alkoxycarbonylalkyl, $C_6$–$C_8$ alkenyloxycarbonylalkyl, $C_6$–$C_8$ alkynyloxycarbonylalkyl, $C_5$–$C_8$ alkoxycarbonylalkenyl, $C_4$–$C_8$ alkenyloxyalkyl, $C_6$–$C_8$ cycloalkoxyalkyl, $C_4$–$C_8$ alkynyloxyalkyl, $C_3$–$C_8$ haloalkoxyalkyl, $C_4$–$C_8$ haloalkenyloxyalkyl, $C_4$–$C_8$ haloalkynyloxyalkyl, $C_4$–$C_8$ alkenylthioalkyl, $C_4$–$C_8$ alkynylthioalkyl; $C_1$–$C_4$ alkyl substituted with phenoxy or benzyloxy, each of the phenoxy and benzyloxy optionally substituted with at least one member independently selected from the group halogen, $C_1$–$C_3$ alkyl and $C_1$–$C_3$ haloalkyl, $C_4$–$C_8$ trialkylsilylalkyl, $C_3$–$C_8$ cyanoalkyl, $C_3$–$C_8$ halocycloalkyl, $C_3$–$C_8$ haloalkenyl, $C_5$–$C_8$ alkoxyalkenyl, $C_5$–$C_8$ haloalkoxyalkenyl, $C_5$–$C_8$ alkylthioalkenyl, $C_3$–$C_8$ haloalkynyl, $C_5$–$C_8$ alkoxyalkynyl, $C_5$–$C_8$ haloalkoxyalkynyl, $C_5$–$C_8$ alkylthioalkynyl, $C_2$–$C_8$ alkylcarbonyl; benzyl optionally substituted with at least one member independently selected from the group halogen, $C_1$–$C_3$ alkyl and $C_1$–$C_3$ haloalkyl; $CHR^{17}COR^{18}$, $CHR^{17}P(O)(ORl^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl and pyridyl, each of the phenyl and pyridyl optionally substituted with at least one member independently selected from the group halogen, $C_1$–$C_3$ alkyl, $C_1$–$C_3$ haloalkyl, $C_1$–$C_4$ alkoxy and $CHR^{17}CH=NOR^{18}$;

$R^{12}$ and $R^{14}$ are independently hydrogen or $C_1$–$C_4$ alkyl;
$R^{13}$ and $R^{15}$ are independently selected from the group $C_1$–$C_4$ alkyl and phenyl optionally substituted with at least one member independently selected from the group halogen, $C_1$–$C_3$ alkyl, $C_1$–$C_3$ haloalkyl and $C_1$–$C_4$ alkoxy; or $R^{12}$ and $R^{13}$ are taken together as —$(CH_2)_5$—, —$(CH_2)_4$— or —$CH_2CH_2OCH_2CH_2$—, each independently forming a ring in which one or more H atoms is optionally replaced by at least one member independently selected from the group $C_1$–$C_3$ alkyl, optionally substituted phenyl and optionally substituted benzyl; or $R^{14}$ and $R^{15}$ together with the carbon atom to which they are attached is $C_3$–$C_8$ cycloalkyl;
$R^{16}$ is $C_1$–$C_4$ alkyl or $C_1$–$C_4$ haloalkyl;
$R^{17}$ is hydrogen or $C_1$–$C_3$ alkyl;
$R^{18}$ is selected from the group $C_1$–$C_6$ alkyl, $C_3$–$C_6$ alkenyl and $C_3$–$C_6$ alkynyl; and
q is 1 or 2.

2. A compound according to claim 1, wherein:
X is group O;
$R^4$ is independently selected from the group fluorine, chlorine and bromine;

51

$R^5$ is selected from the group hydrogen, fluorine and chlorine;

$R^6$ is selected from the group chlorine, bromine and cyano;

$R^7$ is selected from the group hydrogen, $OR^{11}$, $CO_2R^{11}$, $C_1$–$C_2$ alkyl and $C_1$–$C_2$ haloalkyl;

$R^{10}$ is selected from the group $C_1$–$C_2$ alkyl, $C_1$–$C_2$ haloalkyl, $C_3$–$C_4$ alkenyl and $C_3$–$C_4$ alkynyl;

$R^{11}$ is selected from the group $C_1$–$C_4$ alkyl, $C_3$–$C_6$ cycloalkyl, $C_3$–$C_6$ alkenyl, $C_3$–$C_6$ alkynyl, $C_1$–$C_4$ haloalkyl, $C_2$–$C_4$ alkoxyalkyl, $C_2$–$C_4$ alkylthioalkyl, $C_2$–$C_4$ alkylsulphinylalkyl, $C_2$–$C_4$ alkylsulphonylalkyl, $C_3$–$C_6$ alkoxyalkoxyalkyl, $C_4$–$C_8$ cycloalkylalkyl, $C_2$–$C_4$ carboxyalkyl, $C_3$–$C_6$ alkoxycarbonylalkyl, $C_6$–$C_8$ alkenyloxycarbonylalkyl, $C_6$–$C_8$ alkynyloxycarbonylalkyl, $C_5$–$C_6$ alkoxycarbonylalkenyl, $C_6$–$C_8$ cycloalkoxyalkyl, $C_4$–$C_6$ alkenyloxyalkyl, $C_4$–$C_6$ alkynyloxyalkyl, $C_3$–$C_6$ haloalkoxyalkyl, $C_4$–$C_8$ haloalkenoxyalkyl, $C_4$–$C_6$ haloalkynyloxyalkyl, $C_6$–$C_8$ cycloalkylthioalkyl, $C_4$–$C_6$ alkenylthioalkyl, $C_4$–$C_6$ alkynylthioalkyl; $C_1$–$C_2$ alkyl substituted with phenoxy or benzyloxy, each of the phenoxy and benzyloxy optionally substituted with at least one member independently selected from the group halogen, $C_1$–$C_3$ alkyl and $C_1$–$C_3$ haloalkyl; $C_4$–$C_8$ trialkylsilylalkyl, $C_3$–$C_4$ cyanoalkyl, $C_3$–$C_6$ halocycloalkyl, $C_3$–$C_6$ haloalkenyl, $C_5$–$C_6$ alkoxyalkenyl, $C_5$–$C_6$ haloalkoxyalkenyl, $C_5$–$C_6$ alkylthioalkenyl, $C_3$–$C_6$ haloalkynyl, $C_5$–$C_6$ alkoxyalkynyl, $C_5$–$C_6$ haloalkoxyalkynyl, $C_5$–$C_6$ alkylthioalkynyl, $C_2$–$C_4$ alkylcarbonyl, benzyl optionally substituted with at least one member independently selected from the group halogen, $C_1$–$C_2$ alkyl and $C_1$–$C_2$ haloalkyl; $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl and pyridyl, each of the phenyl and pyridyl optionally substituted with at least one member independently selected from the group fluorine, chlorine, bromine, $C_1$–$C_2$ alkylhaloalkyl and $C_1$–$C_2$ alkoxy;

$R^{12}$ is hydrogen or $C_1$–$C_2$ alkyl;

$R^{13}$ is selected from the group $C_1$–$C_2$ alkyl and phenyl optionally substituted with at least one member selected from the group fluorine, chlorine, bromine, $C_1$–$C_2$ alkyl, $C_1$–$C_2$ haloalkyl and $C_1$–$C_2$ alkoxy; or $R^{12}$ and $R^{13}$ are taken together as —$(CH_2)_5$—, —$(CH_2)_4$— or —$CH_2CH_2OCH_2CH_2$—, each independently forming a ring in which one or more H atoms is optionally and independently replaced by $C_1$–$C_2$ alkyl;

$R^{17}$ is hydrogen or $C_1$–$C_2$ alkyl; and $R^{18}$ is selected from the group $C_1$–$C_2$ alkyl, $C_3$–$C_4$ alkenyl and $C_3$–$C_4$ alkynyl.

3. A process for making a compound of Formula I

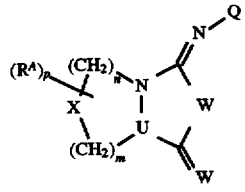

I wherein:

X is selected from the group O, S, S(O), $S(O)_2$, $CH_2$, CHF, $CF_2$, CHCl, CHBr, $CHOCH_2F$, $CHOCHF_2$, $CHOCF_3$, $CHOCH_2CF_3$ and $NR^4$;

52 m and n are independently 1 or 2, where m+n=2 or 3;

p is 0 to 9;

U is N or CH;

W is independently O or S;

$R^A$ is independently selected from the group halogen, $C_1$–$C_4$ alkyl, cyano, $C_1$–$C_4$ haloalkyl, $C_3$–$C_4$ alkenyl, $C_1$–$C_3$ alkylthio, $C_1$–$C_3$ haloalkylthio, $C_2$–$C_4$ alkylcarbonyl, $OR^3$, $C_2$–$C_6$ alkyloxycarbonyl, $C_2$–$C_6$ haloalkoxycarbonyl, and $C_3$–$C_8$ alkoxycarbonylalkyl; or, two $R^A$ groups on the same carbon atom, together with this carbon, are C=O;

$R^3$ is selected from the group hydrogen, $C_1$–$C_4$ alkyl, $C_1$–$C_4$ haloalkyl, $C_2$–$C_4$ alkylcarbonyl and $C_2$–$C_4$ haloalkylcarbonyl;

$R^4$ is selected from the group hydrogen, $C_1$–$C_3$ alkyl, $C_1$–$C_3$ haloalkyl, $C_2$–$C_4$ alkylcarbonyl, $C_2$–$C_4$ haloalkoxycarbonyl and $C_2$–$C_4$ alkoxycarbonyl;

Q is selected from the group

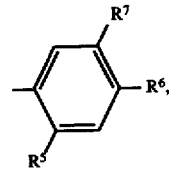

Q-1

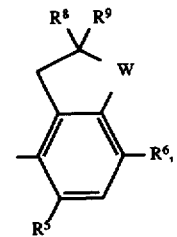

Q-2

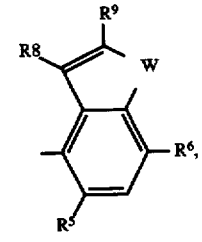

Q-3

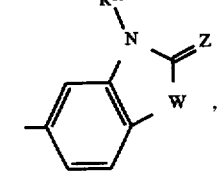

Q-4

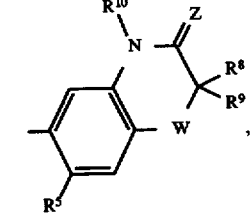

Q-5

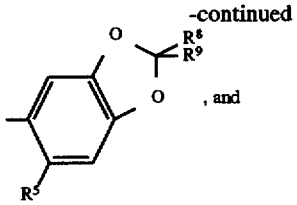

Q-6

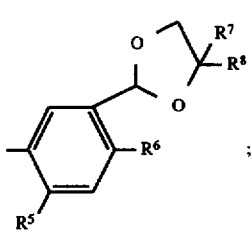

Q-7

Z is O or S;

R⁵ is hydrogen or halogen;

R⁶ is selected from the group $C_1$–$C_2$ alkyl, $C_1$–$C_2$ haloalkyl, $OCH_3$, $SCH_3$, $OCHF_2$, halogen, CN and $NO_2$;

R⁷ is selected from the group hydrogen, $C_1$–$C_8$ alkyl, $C_1$–$C_8$ haloalkyl, halogen, $OR^{11}$, $SR^{11}$, $S(O)_qR^{11}$, $COR^{11}$, $CO_2R^{11}$, $C(O)SR^{11}$, $C(O)NR^{12}R^{13}$, CHO and $NHSO_2NHR^{16}$;

R⁸ is selected from the group hydrogen, $C_1$–$C_3$ alkyl, $C_1$–$C_3$ haloalkyl and halogen;

R⁹ is selected from the group hydrogen, $C_1$–$C_3$ alkyl, $C_1$–$C_3$ haloalkyl and halogen; or, when Q is Q-2 or Q-6, R⁸ and R⁹ together with the carbon to which they are bonded is additionally selected from C=O;

R¹⁰ is selected from the group $C_1$–$C_6$ alkyl, $C_1$–$C_6$ haloalkyl, $C_2$–$C_6$ alkoxyalkyl, $C_3$–$C_6$ alkenyl and $C_3$–$C_6$ alkynyl;

R¹¹ is selected from the group $C_1$–$C_8$ alkyl, $C_3$–$C_8$ cycloalkyl, $C_3$–$C_8$ alkenyl, $C_3$–$C_8$ alkynyl, $C_1$–$C_8$ haloalkyl, $C_2$–$C_8$ alkoxyalkyl, $C_2$–$C_8$ alkylthioalkyl, $C_2$–$C_8$ alkylsulphinylalkyl, $C_2$–$C_8$ alkylsulphonylalkyl, $C_3$–$C_8$ alkoxyalkoxyalkyl, $C_4$–$C_8$ cycloalkylalkyl, $C_2$–$C_4$ carboxyalkyl, $C_3$–$C_8$ alkoxycarbonylalkyl, $C_6$–$C_8$ alkenyloxycarbonylalkyl, $C_6$–$C_8$ alkynyloxycarbonylalkyl, $C_5$–$C_8$ alkoxycarbonylalkenyl, $C_4$–$C_8$ alkenyloxyalkyl, $C_6$–$C_8$ cycloalkoxyalkyl, $C_4$–$C_8$ alkynyloxyalkyl, $C_3$–$C_8$ haloalkoxyalkyl, $C_4$–$C_8$ haloalkenyloxyalkyl, $C_4$–$C_8$ haloalkynyloxyalkyl, $C_4$–$C_8$ alkenylthioalkyl, $C_4$–$C_8$ alkynylthioalkyl; $C_1$–$C_4$ alkyl substituted with phenoxy or benzyloxy, each of the phenoxy and benzyloxy optionally substituted with at least one member independently selected from the group halogen, $C_1$–$C_3$ alkyl and $C_1$–$C_3$ haloalkyl, $C_4$–$C_8$ trialkylsilylalkyl, $C_3$–$C_8$ cyanoalkyl, $C_3$–$C_8$ halocycloalkyl, $C_3$–$C_8$ haloalkenyl, $C_5$–$C_8$ alkoxyalkenyl, $C_5$–$C_8$ haloalkoxyalkenyl, $C_5$–$C_8$ alkylthioalkenyl, $C_3$–$C_8$ haloalkynyl, $C_5$–$C_8$ alkoxyalkynyl, $C_5$–$C_8$ haloalkoxyalkynyl, $C_5$–$C_8$ alkylthioalkynyl, $C_2$–$C_8$ alkylcarbonyl; benzyl optionally substituted with at least one member independently selected from the group halogen, $C_1$–$C_3$ alkyl and $C_1$–$C_3$ haloalkyl; $CHR^{17}COR^{18}$, $CHR^7P(O)(ORI^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl and pyridyl, each of the phenyl and pyridyl optionally substituted with at least one member independently selected from the group halogen, $C_1$–$C_3$ alkyl, $C_1$–$C_3$ haloalkyl, $C_1$–$C_4$ alkoxy and $CHR^{17}CH=NOR^{18}$;

R¹² and R¹⁴ are independently hydrogen or $C_1$–$C_4$ alkyl;

R¹³ and R¹⁵ are independently selected from the group $C_1$–$C_4$ alkyl and phenyl optionally substituted with at least one member independently selected from the group halogen, $C_1$–$C_3$ alkyl, $C_1$–$C_3$ haloalkyl and $C_1$–$C_4$ alkoxy; or R¹² and R¹³ are taken together as —$(CH_2)_5$—, —$(CH_2)_4$— or —$CH_2CH_2OCH_2CH_2$—, each independently forming a ring in which one or more H atoms is optionally replaced by at least one member independently selected from the group $C_1$–$C_3$ alkyl, optionally substituted phenyl and optionally substituted benzyl; or R¹⁴ and R¹⁵ together with the carbon atom to which they are attached is $C_3$–$C_8$ cycloalkyl;

R¹⁶ is $C_1$–$C_4$ alkyl or $C_1$–$C_4$ haloalkyl;

R¹⁷ is hydrogen or $C_1$–$C_3$ alkyl;

R¹⁸ is selected from the group $C_1$–$C_6$ alkyl, $C_3$–$C_6$ alkenyl and $C_3$–$C_6$ alkynyl; and q is 1 or 2 comprising one of the following steps:

a) reacting a compound of Formula II with a compound of Formula III,

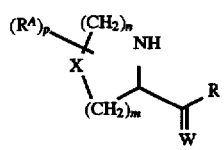

III

Q—NCW

II wherein R=hydroxy, $C_1$–$C_4$ alkoxy, halogen or O-active ester, optionally in the presence of a solvent;

b) reacting a compound of Formula IV,

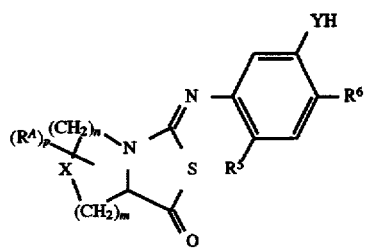

IV wherein Y is selected from the group O, S and NH, with a compound of Formula V, VI or VII, $R^{11}$—Z      V
$R^{16}SO_2$—Z      VI
$R^{16}NHSO_2$—Z      VII wherein Z is selected from the group chlorine, bromine, iodine, O—$SO_2CH_3$, O—$SO_2CF_3$, O—$SO_2$—Ph, and

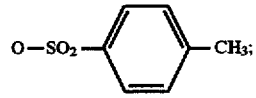

c) reacting a compound of Formula III first with a compound of Formula XV, wherein $L^1$ and $L^2$ are independently selected leaving groups, to form a compound of Formula VIII, then, with a compound of Formula IX to form a compound of Formula X,

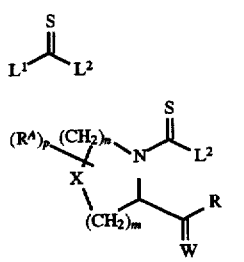

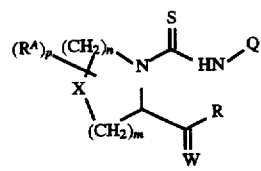

and cyclizing the compound of Formula X; and d) reacting a compound of Formula XI with a compound of Formula XVb optionally in the presence of a diluent and optionally in the presence of an acid-acceptor.

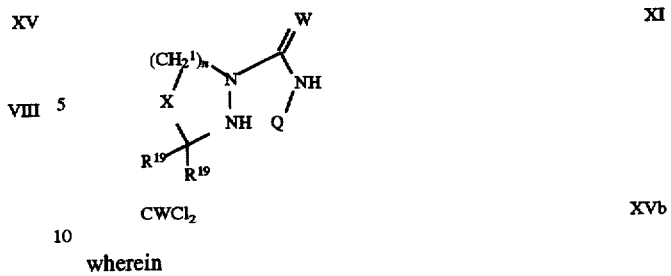

wherein $R^1$ is independently H or $R^A$; and $R^{19}$ is independently selected from the group H, $C_1$–$C_4$ alkyl, $C_1$–$C_4$ haloalkyl, and $C_3$–$C_4$ alkenyl.

4. A herbicidal composition comprising an herbicidally effective mount of a compound according to claim 1 and a carrier therefor.

5. A method of controlling unwanted vegetation comprising applying to the unwanted vegetation or the environment in which it is grown an herbicidally effective amount of a compound according to claim 1.

* * * * *